United States Patent
Burns et al.

(10) Patent No.: US 7,996,076 B2
(45) Date of Patent: Aug. 9, 2011

(54) AUTOMATED POLYSOMNOGRAPHIC ASSESSMENT FOR RAPID EYE MOVEMENT SLEEP BEHAVIOR DISORDER

(75) Inventors: Joseph W. Burns, Ann Arbor, MI (US); Ronald D. Chervin, Ann Arbor, MI (US)

(73) Assignees: The Regents of the University of Michigan, Ann Arbor, MI (US); Michigan Technological University, Houghton, MI (US)

( * ) Notice: Subject to any disclaimer, the term of this patent is extended or adjusted under 35 U.S.C. 154(b) by 683 days.

(21) Appl. No.: 12/080,440

(22) Filed: Apr. 2, 2008

(65) Prior Publication Data

US 2008/0262373 A1 Oct. 23, 2008

Related U.S. Application Data

(60) Provisional application No. 60/921,466, filed on Apr. 2, 2007.

(51) Int. Cl.
*A61B 5/00* (2006.01)
*A61B 5/04* (2006.01)

(52) U.S. Cl. ......... 600/546; 600/300; 600/544; 600/545

(58) Field of Classification Search .................. 600/300, 600/544–546
See application file for complete search history.

(56) References Cited

U.S. PATENT DOCUMENTS

| | | | | |
|---|---|---|---|---|
| 5,732,696 A * | 3/1998 | Rapoport et al. | ............. | 600/301 |
| 6,419,629 B1 * | 7/2002 | Balkin et al. | ................ | 600/300 |
| 6,530,884 B2 * | 3/2003 | Balkin et al. | ................ | 600/300 |
| 6,553,252 B2 * | 4/2003 | Balkin et al. | ................ | 600/544 |
| 6,740,032 B2 * | 5/2004 | Balkin et al. | ................ | 600/300 |
| 7,190,995 B2 * | 3/2007 | Chervin et al. | ............... | 600/544 |
| 7,578,793 B2 * | 8/2009 | Todros et al. | ................ | 600/484 |
| 7,623,912 B2 * | 11/2009 | Akselrod et al. | ............. | 600/513 |
| 7,717,848 B2 * | 5/2010 | Heruth et al. | ................ | 600/300 |
| 7,766,827 B2 * | 8/2010 | Balkin et al. | ................ | 600/300 |
| 7,774,052 B2 * | 8/2010 | Burton et al. | ................ | 600/544 |
| 2001/0021800 A1 * | 9/2001 | Balkin et al. | ................ | 600/300 |
| 2002/0017994 A1 * | 2/2002 | Balkin et al. | ............. | 340/573.1 |
| 2003/0163027 A1 * | 8/2003 | Balkin et al. | ................ | 600/137 |
| 2004/0097802 A1 * | 5/2004 | Cohen | .......................... | 600/411 |
| 2004/0193068 A1 * | 9/2004 | Burton et al. | ................ | 600/544 |

(Continued)

OTHER PUBLICATIONS

Canisius S., et al., Entitled: Automatic Analysis of Muscle Activity for the Investigation of REM Sleep Behavior Disorder; SLEEP, vol. 30, Abstract Suppl.; Jun. 9-14, 2007; p. A342.

(Continued)

*Primary Examiner* — Max Hindenburg
*Assistant Examiner* — Sean P Dougherty
(74) *Attorney, Agent, or Firm* — Harness, Dickey & Pierce, P.L.C.

(57) ABSTRACT

Methods and systems for diagnosing or assessing rapid eye movement sleep behavior disorder (RBD). Muscle tone or activity variance during rapid eye movement (REM) and non-rapid eye movement (NREM) sleep intervals of a polysomnogram are compared. A threshold based on the NREM data is used to identify a subject-specific threshold for abnormality in the REM variance. A metric that includes the percentage of REM variance exceeding the threshold relates to RBD.

24 Claims, 11 Drawing Sheets

U.S. PATENT DOCUMENTS

| | | | |
|---|---|---|---|
| 2005/0033122 A1* | 2/2005 | Balkin et al. | 600/300 |
| 2005/0061319 A1* | 3/2005 | Hartley et al. | 128/204.18 |
| 2005/0061320 A1* | 3/2005 | Lee et al. | 128/204.18 |
| 2005/0124864 A1* | 6/2005 | Mack et al. | 600/300 |
| 2005/0267362 A1* | 12/2005 | Mietus et al. | 600/429 |
| 2006/0111635 A1* | 5/2006 | Todros et al. | 600/484 |
| 2006/0235315 A1* | 10/2006 | Akselrod et al. | 600/509 |
| 2007/0055115 A1* | 3/2007 | Kwok et al. | 600/300 |
| 2007/0208269 A1* | 9/2007 | Mumford et al. | 600/546 |
| 2007/0270706 A1* | 11/2007 | Merilainen et al. | 600/544 |
| 2008/0154111 A1* | 6/2008 | Wu et al. | 600/383 |
| 2008/0190430 A1* | 8/2008 | Melker et al. | 128/204.23 |
| 2009/0292215 A1* | 11/2009 | Todros et al. | 600/484 |
| 2010/0076333 A9* | 3/2010 | Burton et al. | 600/544 |

OTHER PUBLICATIONS

Bliwise, Donald L., et al., Entitled: Quantification of Electromyographic Activity During Sleep: A Phasic Electromyographic Metric; Journal of Clinical Neurophysiology; vol. 23, No. 1; Feb. 2006; pp. 59-67.

Lapierre, Odile, et al., Entitled: Polysomnographic Features of REM Sleep Behavior Disorder: Development of a Scoring Method; Neurolgy 1992; 42; pp. 1371-1374.

Consens, Flavia B., MD, et al. Entitled: Validation of a Polysomnographic Score for REM Sleep Disorder; SLEEP, vol. 28, No. 8; 2005; pp. 993-997.

* cited by examiner

US 7,996,076 B2

AUTOMATED POLYSOMNOGRAPHIC ASSESSMENT FOR RAPID EYE MOVEMENT SLEEP BEHAVIOR DISORDER

CROSS-REFERENCE TO RELATED APPLICATIONS

This application claims the benefit of U.S. Provisional Application No. 60/921,466, filed on Apr. 2, 2007. The disclosure of the above application is incorporated herein by reference.

GOVERNMENT RIGHTS

This invention was made with government support under Contract Nos. P01 NS15655 and M01 RR000042 awarded by the National Institutes of Health. The government has rights in the invention.

FIELD

The present disclosure relates to methods and systems for diagnosing and assessing rapid eye movement sleep behavior disorder and related conditions.

INTRODUCTION

Rapid eye movement (REM) sleep behavior disorder (RBD) affects about 0.4% of adults, 0.5% of older adults, 33% of patients with newly diagnosed Parkinson's Disease, and 90% of patients with multiple system atrophy. Consequences can include injury to the patient, threats to the safety of a bed partner, and inability to share a bed with a partner. Diagnosis is important because the condition responds well to treatment, most often with clonazepam. Moreover, RBD may be a harbinger for neurodegenerative conditions such as Parkinson's disease (PD), multiple system atrophy (MSA), or dementia with Lewy bodies (DLB), which together comprise the alpha-synucleinopathies. In the absence of RBD, REM sleep without atonia may also signal increased risk for alpha-synucleinopathies.

There is a need for improved methods and systems for the diagnosis of RBD, and for assessment of RBD-like features that may predict future development of neurodegenerative disorders. The statements in this section merely provide background information related to the present disclosure and may not constitute prior art.

SUMMARY

The present disclosure includes methods and systems related to assessment of rapid eye movement sleep behavior disorder and related conditions.

In some embodiments, the present disclosure relates to a method for diagnosing and assessing rapid eye movement sleep behavior disorder (RBD) in a patient. The method includes measuring at least one physiological signal of the patient during at least one rapid eye movement (REM) sleep time interval and at least one non-rapid eye movement (NREM) sleep time interval. The method also includes determining a Variance for the physiological signal within at least one REM sleep time interval and a variance for the physiological signal within at least one NREM sleep time interval. A threshold based on the NREM variance is established and a percentage of REM sleep time intervals with variance above the threshold is calculated. The patient may be classified as an RBD candidate when the percentage exceeds the threshold during the REM sleep time interval or the percentage may be used in conjunction with a visual PSG score and/or clinical impression to assess RBD.

Further areas of applicability will become apparent from the description provided herein. It should be understood that the description and specific examples are intended for purposes of illustration only and are not intended to limit the scope of the present disclosure.

DRAWINGS

Figure 3:
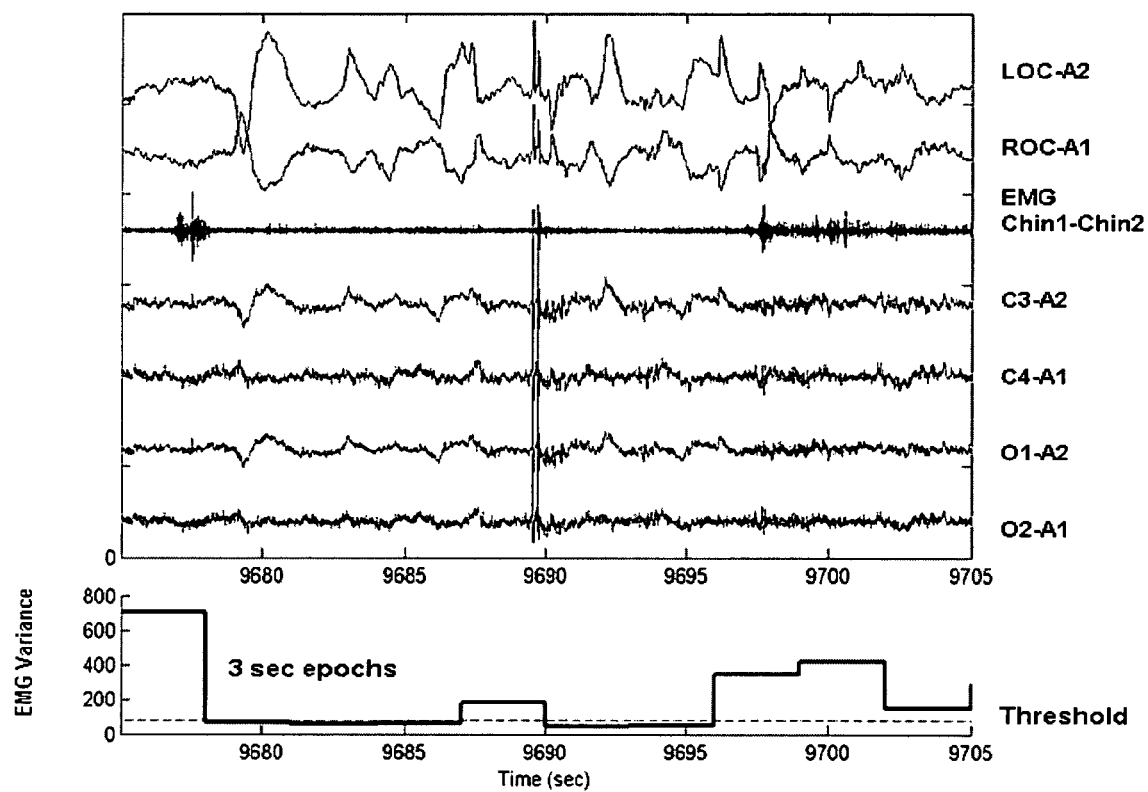
Figure 4A:
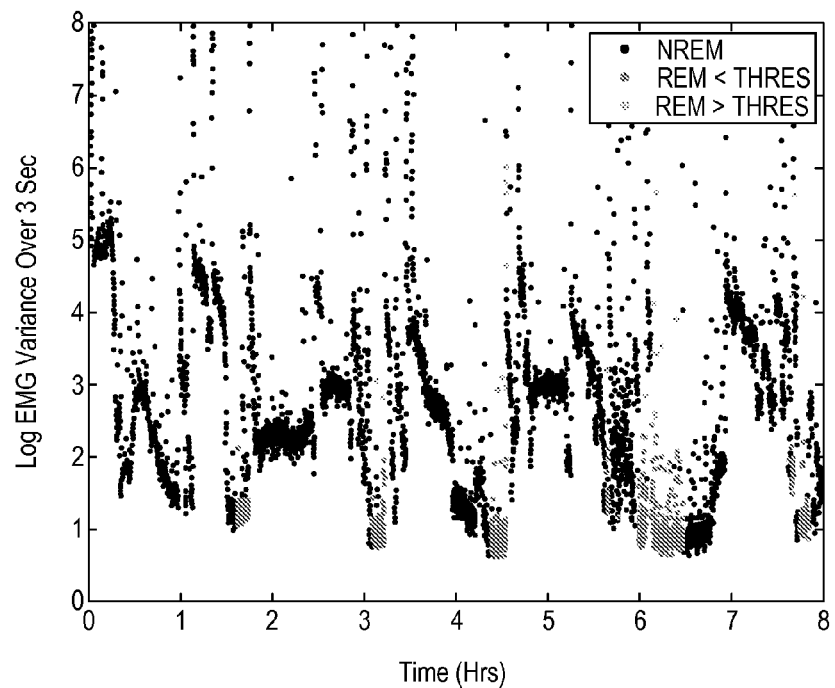
Figure 4B:
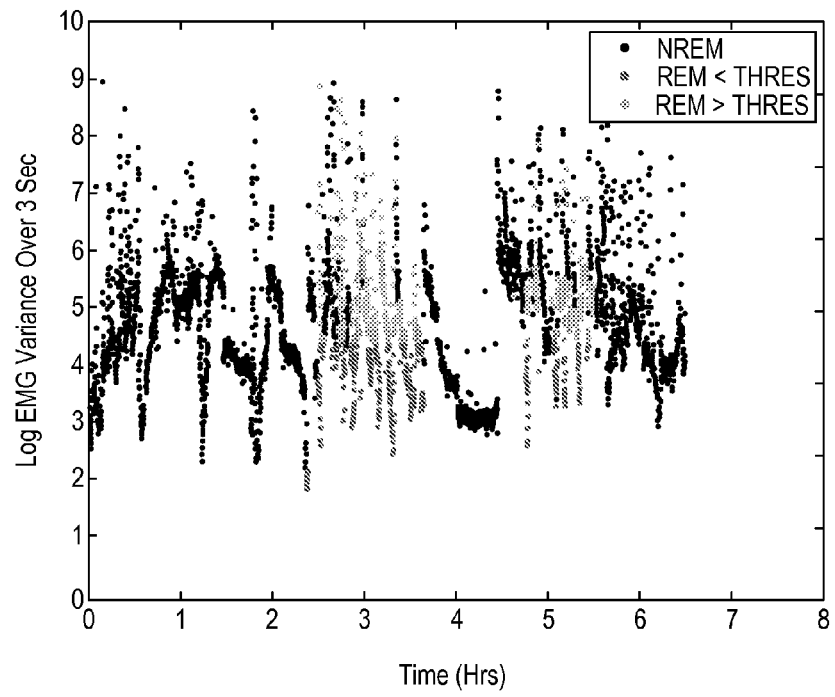
Figure 5:
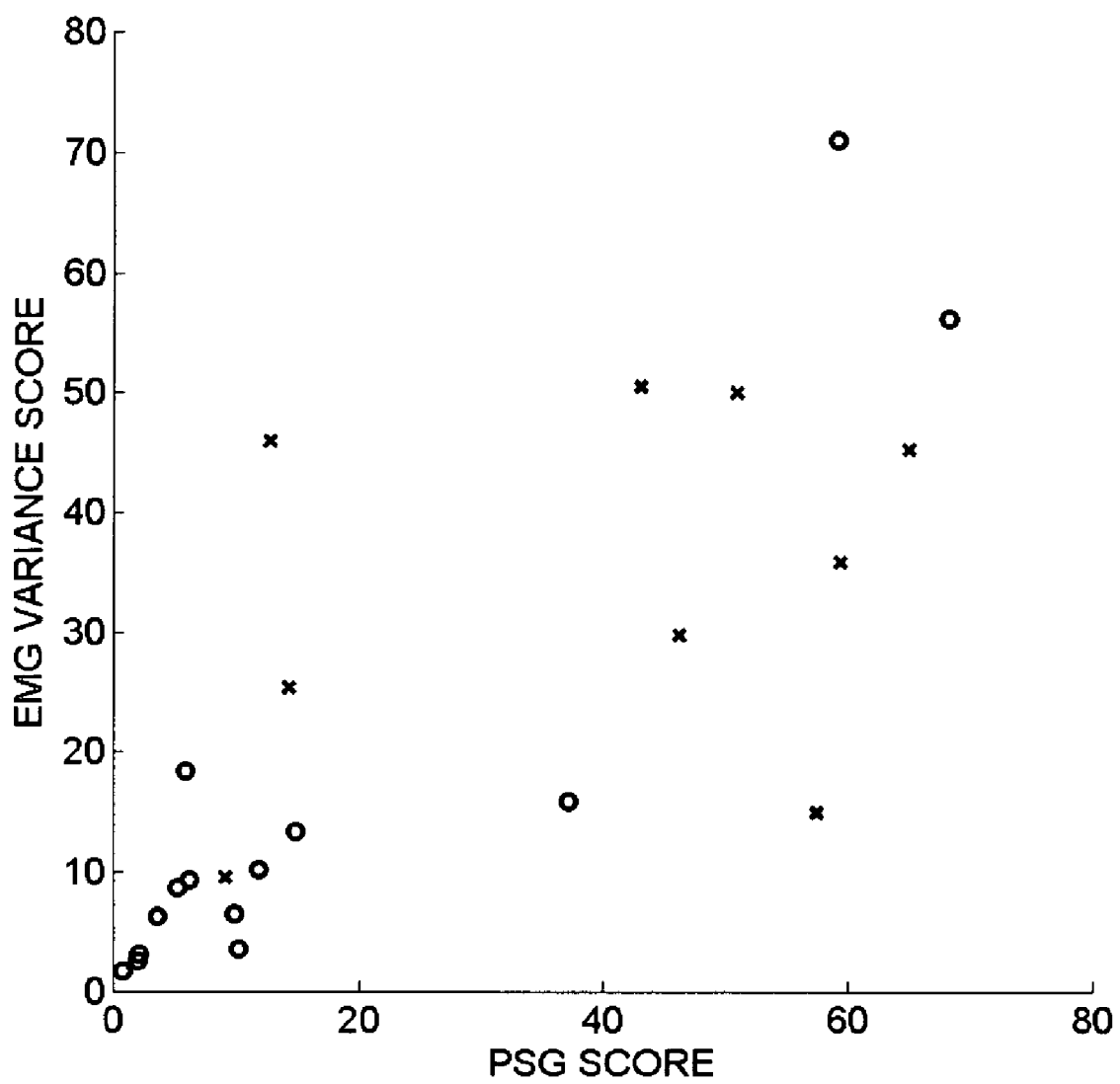
Figures 6A, 6B:
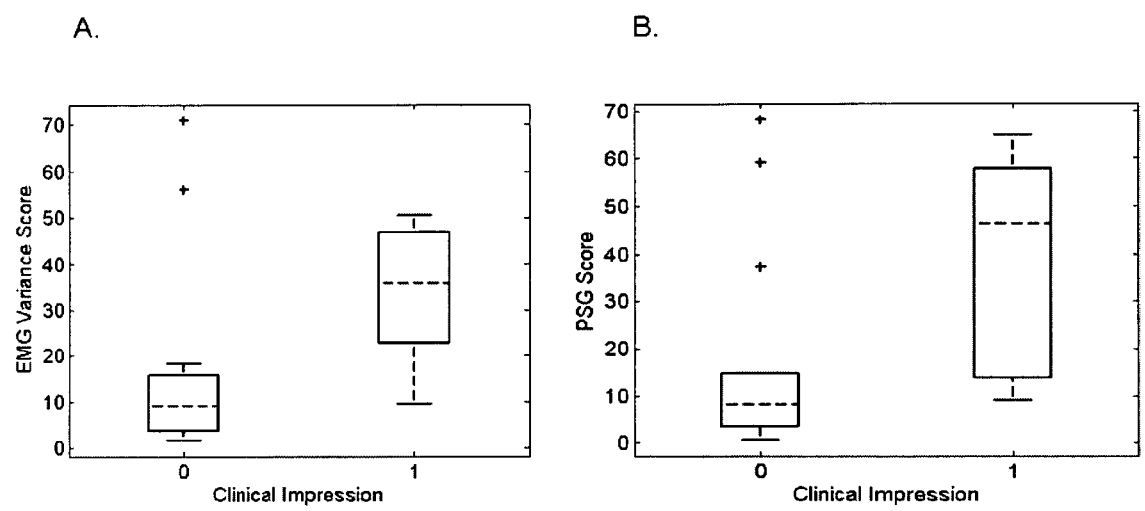
Figure 8:
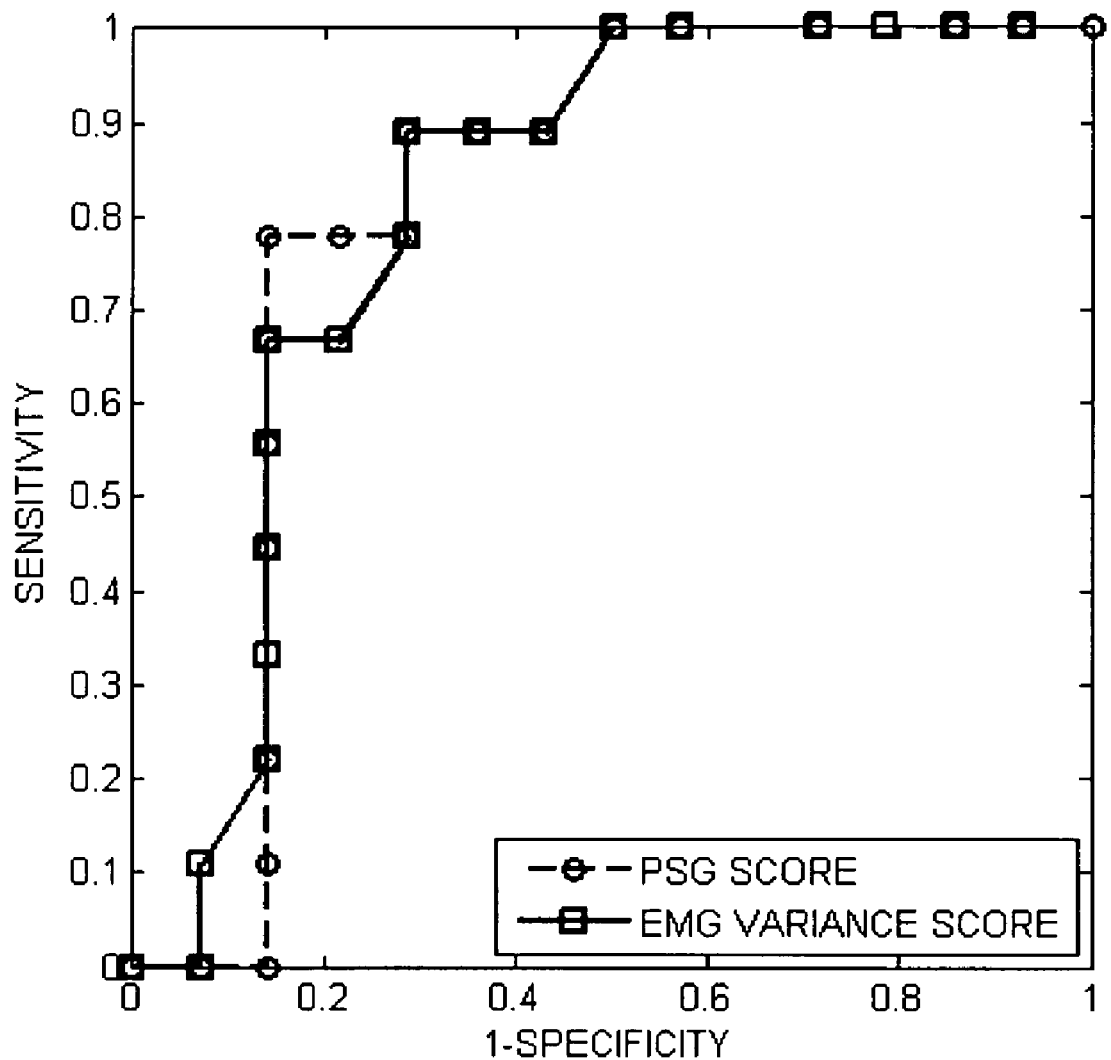
Figure 9:
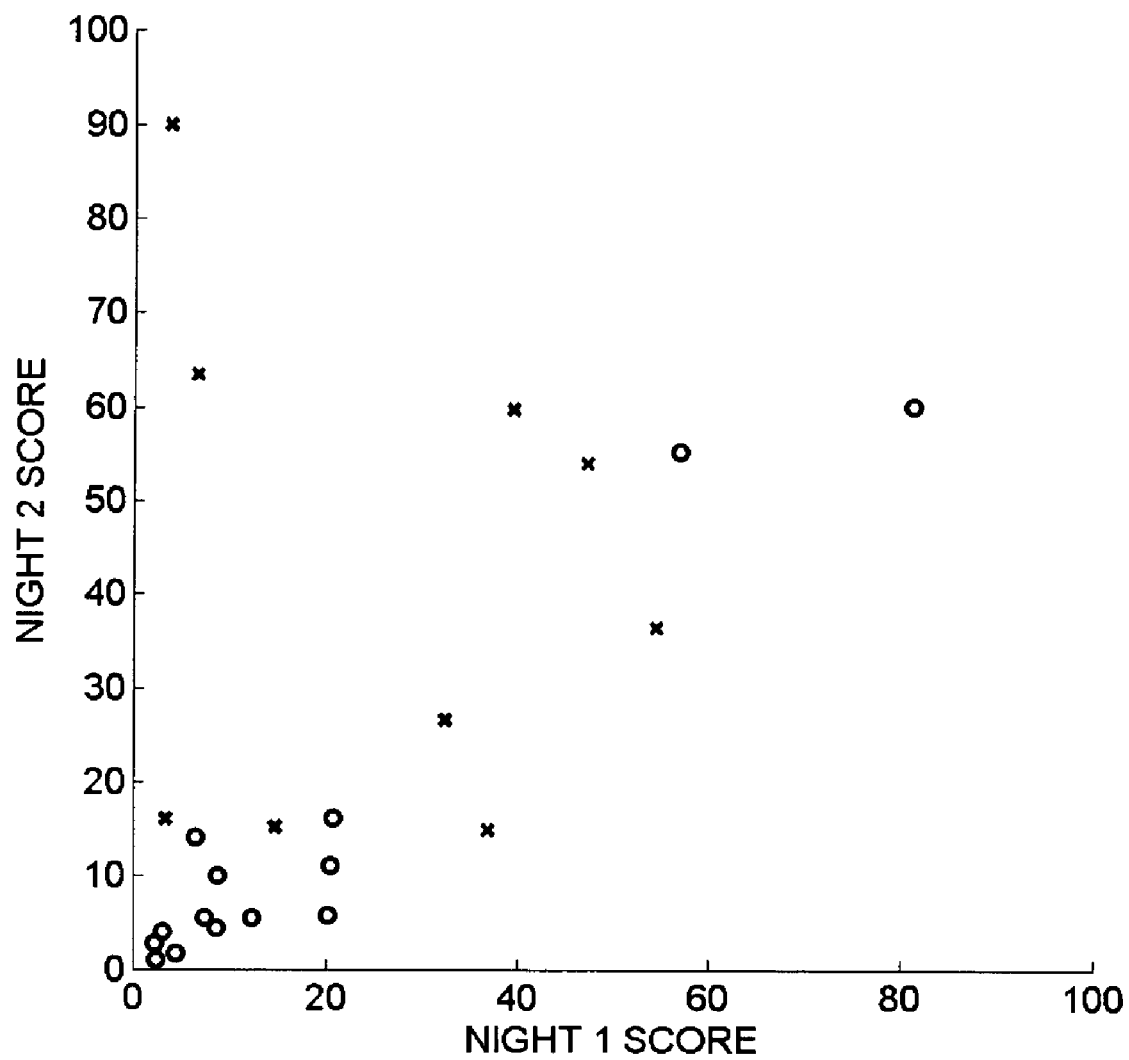
Figure 10:
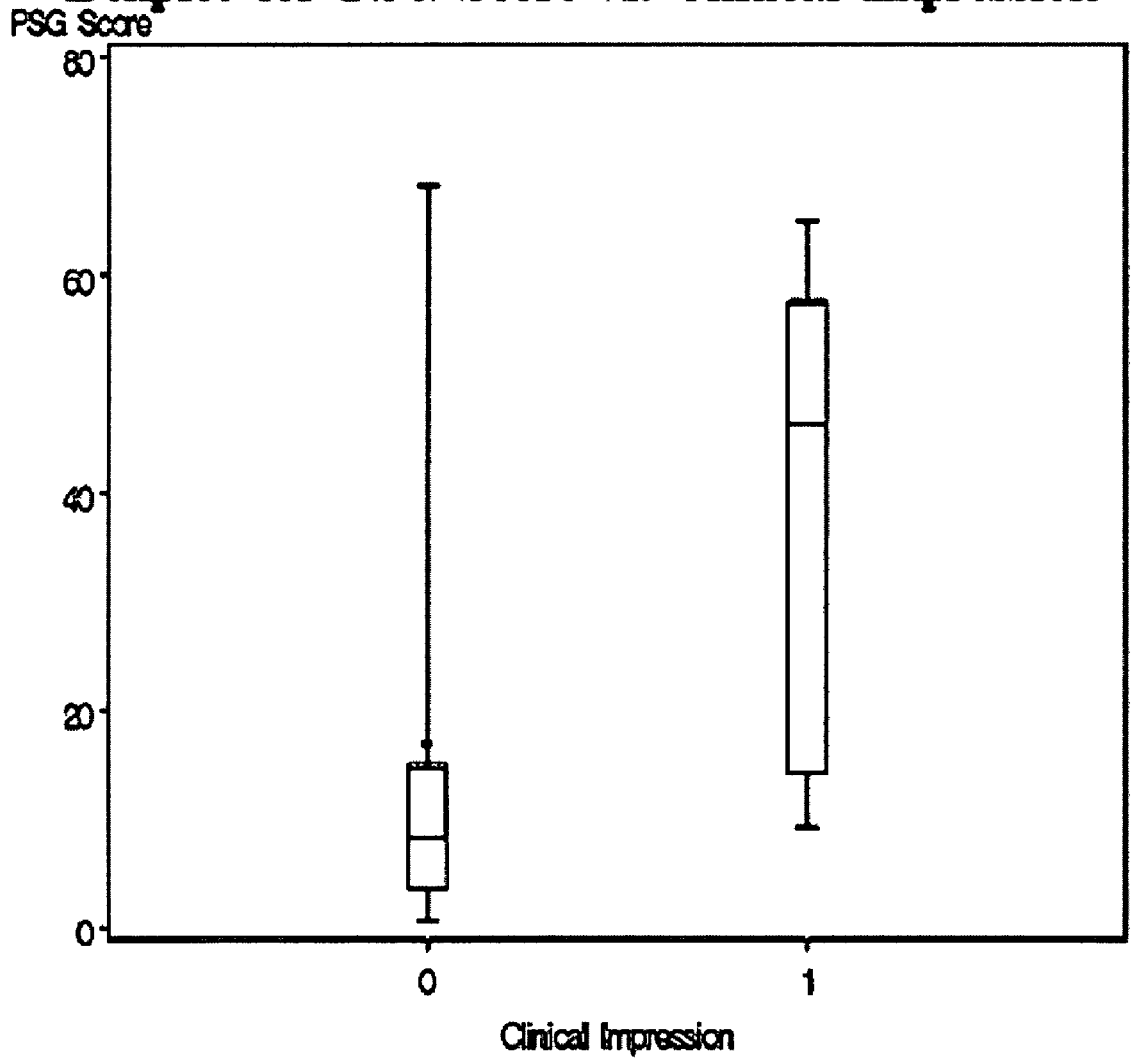
Figure 11:
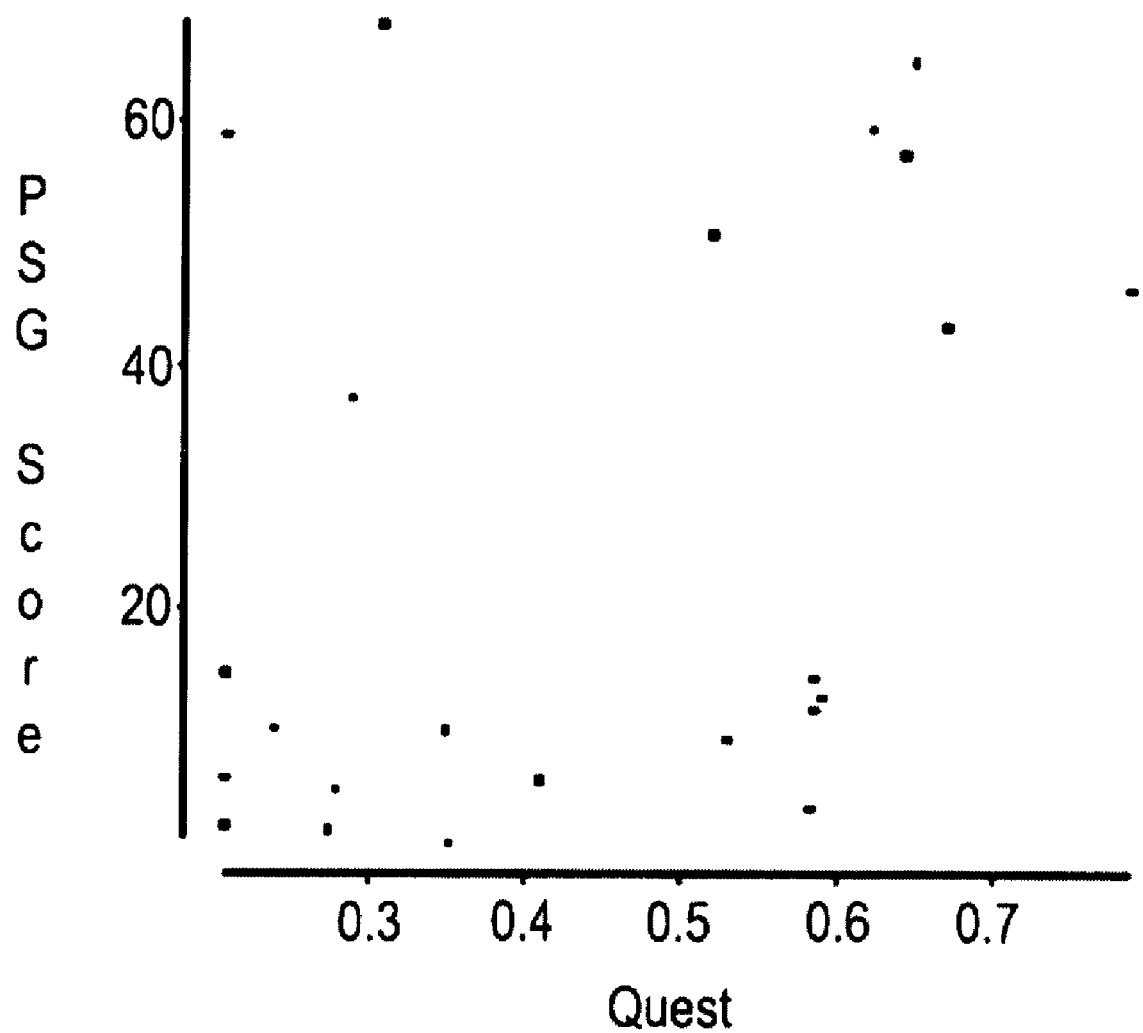

FIG. 3 graphically illustrates a thirty-second epoch of REM sleep (upper panel), along with a corresponding plot of calculated EMG variance for each 3-second mini-epoch (lower panel);

FIG. 4 graphically illustrates electromyographic variance computed over 3-second mini-epochs through the night (A) for a subject without a clinical diagnosis of RBD, and (B) for a subject with a clinical diagnosis of RBD;

FIG. 5 graphically illustrates that the computer-generated Supra-Threshold REM EMG Activity Metric (STREAM) correlates closely with the visually-based polysomnographic score for RBD severity;

FIG. 6 graphically illustrates that the computer-generated EMG variance score (A) and visually-generated PSG score (B) show similar ability to separate subjects for whom RBD was considered probable or possible (1) or unlikely (0) by clinicians who interviewed and examined the subjects;

FIG. 7 graphically illustrates RBD symptom scores derived from an International Criteria for Sleep Disorders-based questionnaire plotted against the computer-generated STREAM score (A) and the visually-generated PSG score (B);

FIG. 8 graphically illustrates receiver-operator characteristic (ROC) curves for the STREAM and the visually-generated PSG score;

FIG. 9 graphically illustrates that the STREAM during REM sleep on night 1 correlates with STREAM on night 2;

FIG. 10 graphically illustrates a quantitative visual scoring method where the RBD polysomnographic score (PSG Score) is plotted against the International Classification of Sleep Disorders-based clinical impression of RBD presence (1) or absence (0); and FIG. 11 graphically illustrates a quantitative visual scoring method where the REM (rapid eye movement) sleep behavior disorder (RBD) polysomnographic score (PSG score) is plotted against the RBD symptom score derived from bed partner questionnaires (Quest).

The drawings described herein are for illustration purposes only and are not intended to limit the scope of the present disclosure in any way.

DETAILED DESCRIPTION

Polysomnography is a valuable technique in the diagnosis of rapid eye movement sleep behavior disorder (RBD) and in identifying REM sleep without atonia, but interpretation of the requisite findings can be highly subjective. In many cases, dream enactment is not directly observed in the sleep laboratory. Diagnosis may depend on the polysomnographer's perception of elevated baseline muscle tone or abnormally frequent bursts of discrete muscle activation recorded from the surface electromyogram (EMG) during REM sleep. Diagnosis based on quantification of these EMG patterns, or some objective polysomnographic measure of RBD severity, is less subjective and more reliable.

In some embodiments, the present disclosure provides methods and systems to quantify polysomnographic evidence of RBD severity; to help assess risk for RBD at present; to help assess risk for development of RBD in the future; and/or to help assess the extent to which physiologic features of RBD are present on the polysomnogram. Embodiments may include a computer algorithm to identify EMG features of RBD automatically. The computerized algorithm identifies polysomnographic evidence of RBD as accurately as visual scoring methods, including those performed by a polysomnographer and including the methods described by Lapierre O, Montplaisir J., "Polysomnographic features of REM sleep behavior disorder: Development of a scoring method," Neurology 1992; 42:1371-1374 and Consens F B, Chervin R D, Koeppe R A et al., "Validation of a polysomnographic score for REM sleep behavior disorder," Sleep 2005; 28(8):993-997. The present methods and visual scoring methods show similar correspondence to clinical and questionnaire evidence of RBD.

In some embodiments, an automated method is provided that facilitates objective identification of RBD based on sleep studies, including, for example, polysomnograms. The method may include recording one or more electromyogram (EMG) signals (non-invasive or invasive) for a subject while the subject is sleeping. It is envisioned that other physiological signals indicative of muscle activity during sleep, such as cardiac-related signals, may be used in place of EMG signals.

Portions of the EMG signal(s) that are recorded during REM sleep are identified. For example, 30-second epochs of REM sleep may be identified using a standard visual scoring method. However, REM sleep phases may be identified either in this manner or by using automated signal analysis techniques. For example, an automated method for distinguishing REM and NREM sleep intervals may include using the Morpheus® Clinical Sleep Information System (WideMed, Ltd., Herzliya, Israel). The automated method for distinguishing REM and NREM sleep may be used concurrently with the present methods to collect and process various physiological signals, including one or more of the following: electroencephalogram (EEG), electromyogram (EMG), electrooculogram (EOG), and electrocardiogram (ECG), or other physiological signals indicative of wakefulness, REM sleep, and NREM sleep.

In some embodiments, the EMG signal is partitioned into predefined time increments (e.g., 3 second mini-epochs) and a variance measure is calculated for each time increment. The variance of n data samples $x_i$ may be computed as $$(1/(n-1))\sum_{i=1}^{n}(x_i-\bar{x})^2, \text{ where } \bar{x}=(1/n)\sum_{i=1}^{n}x_i.$$

It is also contemplated that an alternative measure of EMG variability may be used. An abnormality threshold for the EMG signal variance occurring during REM sleep may be established based on the EMG variance observed during the NREM portion of sleep. For example, the abnormality threshold may be set at four times the $5^{th}$ percentile of the variance observed during the NREM time intervals. Normally, EMG tone during REM sleep should not exceed the lowest tone noted during non-REM sleep, operationalized here as the $5^{th}$ percentile of the NREM EMG variance. To identify activity likely to be abnormal, with reference to NREM EMG tone, the abnormality threshold may be set at 4 times the $5^{th}$ percentile. Other cut-offs may perform similarly; e.g., 2 to 6 times the $5^{th}$ percentile. The choice for a specific cut-off is in no way meant to exclude other choices that can reasonably be made without alteration of the underlying methodological concept. This underlying concept is that a patient-specific EMG variance threshold during REM sleep may be automatically computed (rather than visually and subjectively assessed) for an individual patient based on that same patient's muscle tone during sleep more generally, or particularly during non-REM sleep.

In some embodiments, the percentage of REM mini-epochs with variance above the selected threshold is computed as a metric for assessing RBD. The percentage of all REM mini-epochs with variance above this threshold is also referred to in the present disclosure as the Supra-Threshold REM EMG Activity Metric (STREAM), which may be determined for each patient. A score for each patient may be calculated as a REM sleep duration-weighted average of results over the course of two or more nights. However, STREAM may also be determined based on one night of recording, part of one night, or multiple nights. Other methods and techniques that compare and/or contrast the variability of the EMG signal in REM sleep versus NREM sleep may be used. These other methods and techniques may be used to establish a threshold for assessment of RBD. Thus, various means for determining the variability of the EMG signal between REM and NREM sleep can be used in the present methods and systems.

Figure 1:
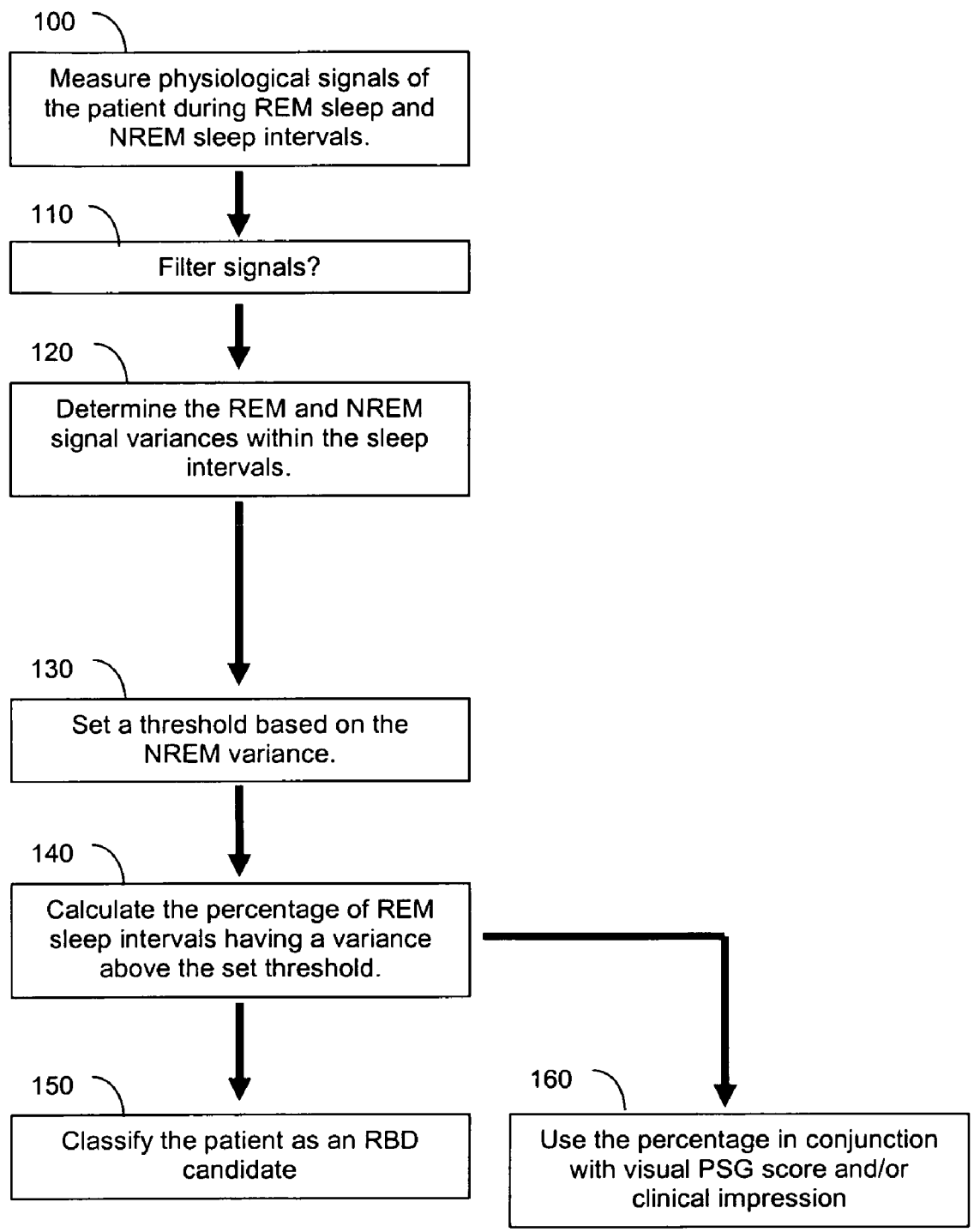
FIG. 1 is a flowchart of a method for diagnosing and assessing rapid eye movement sleep behavior disorder (RBD) in a patient according to one embodiment of the present disclosure.

With reference to FIG. 1, a flowchart is shown that diagrams a method for diagnosing and assessing rapid eye movement sleep behavior disorder (RBD) in a patient. With respect to reference numeral 100, one or more physiological signals of a patient are measured during REM and NREM sleep intervals. These physiological signals may include signals obtained using one or more of the following: electroencephalogram (EEG), electromyogram (EMG), electrooculogram (EOG), electrocardiogram (ECG), snoring, respiratory effort, airflow at the nose and mouth, pulse oximetry, and combinations thereof. In addition to these, other physiological signals that differ between wakefulness, REM sleep, and NREM sleep may be suitable for use in the method; for example, other physiological signals indicative of muscle activity may be used. Signals may also be obtained from multiple locations using the same technique. For example, EMG signals may be measured at the chin, forearm extensor compartments, and the anterior tibialis muscles bilaterally, including surface and/or subsurface measurement.

With respect to reference numeral 110, the physiological signal may be filtered to reduce background noise and/or to select particular frequencies for analysis. Specific EMG frequency bands may prove more useful than others. For example, the lower frequency bands (e.g., 10 to 15 Hz) may be more useful in some cases, and even frequencies lower than 10 Hz may be used.

With respect to reference numeral 120, the time-evolution of the variance is determined for the EMG signal within at least one REM sleep time interval and the background level of the variance is determined for the EMG signal within at least one NREM sleep time interval. These variances may determined by using the formula:

$$\sigma = 1/(N-1) \sum_{i=1}^{N} (x_i - \bar{x})^2$$

wherein σ is the variance, N is the number of samples in the time interval, $x_i$ is the ith sample of the signal in the time interval, and $\bar{x}$ is signal in the time interval. Alternatively, variances may be determined by calculating the sum of the square amplitudes of the physiological signals within the REM sleep time interval. Other techniques for computing the variability of the signal over time are contemplated by this disclosure.

With respect to reference numeral 130, a threshold is established based on the NREM variance. For example, the threshold can be set as the upper limit for the physiological signal background during REM sleep, with the upper limit being about two to about six times the $5^{th}$ percentile of the NREM variance.

With respect to reference numeral 140, a percentage of REM sleep time intervals with variance above the threshold is calculated. For example, where the signals are EMG signals, the method includes calculating the Supra-Threshold REM EMG Activity Metric (STREAM). In addition, various EMG signals may be used, such as EMG signals other than surface chin EMG. The EMG may be recorded from any muscle or multiple muscles, and by means other than surface recordings. It should be appreciated that the calculations described for STREAM in the present disclosure can be applied to determine analogous metrics for various other techniques that measure physiological signals indicative of muscle activity. Thus, when the present disclosure contemplates methods or systems using STREAM, these analogous metrics for muscle activity may be included in addition to or substituted for STREAM.

The percentage or proportion calculated at reference numeral 140 may be used to classify the patient as a candidate for rapid eye movement sleep behavior disorder (RBD), as indicated at reference numeral 150. Alternatively, or in addition to, as shown at reference numeral 160, the percentage or proportion may be used in conjunction with other assessments of RBD, such as visual PSG scoring and/or clinical impressions collected via questionnaires, for example. Alternatively, the percentage or proportion may simply be used as a continuous score for characterization of the subject's physiologic RBD-tendency, rather than as a dichotomous score to label a patient as having or not having RBD.

Figure 2:
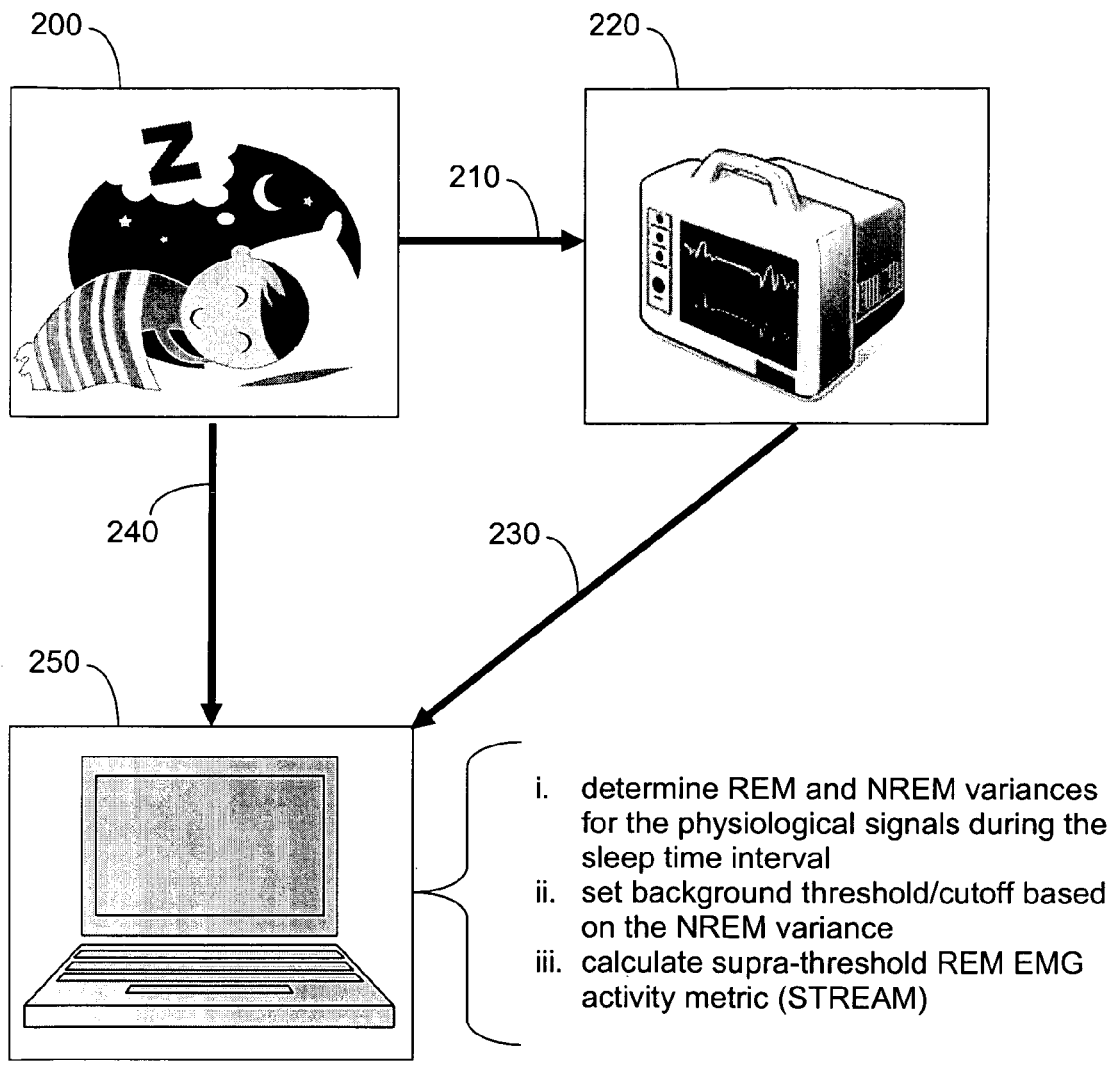
FIG. 2 is a block diagram of a system for diagnosing and assessing rapid eye movement sleep behavior disorder (RBD) in a patient constructed according to one embodiment of the present disclosure.

With reference to FIG. 2, a system is shown for diagnosing and assessing rapid eye movement sleep behavior disorder (RBD) in a patient. The sleeping patient 200 is connected 210 to an instrument 220 that acts as a signal input device to collect one or more physiological signals, for example an electromyograph. The physiological signals may be processed in some manner by the instrument 220. For example, the instrument 220 may filter particular signal frequencies. The instrument 220 (or signal input device) is connected to a processor 250, which as shown in FIG. 2 may be part of a laptop computer. Alternatively, the instrument 220 that collects the signals and the processor 250 may be a single unit, where as shown by reference numeral 240, the physiological signals from the patient 200 are received directly by the combination processor 250 and signal input device.

The processor 250 includes a software-implemented algorithm capable of determining a rapid eye movement (REM) variance for the physiological signals within at least one REM sleep time interval and a non-rapid eye movement (NREM) variance for physiological signals within the at least one NREM sleep time interval, establishing a threshold based on the NREM variance, and calculating a percentage of REM sleep time intervals with variance above the threshold. The time-evolution of the variance may be determined for the EMG signal within at least one REM sleep time interval and the background level of the variance may be determined for the EMG signal within at least one NREM sleep time interval. It is to be understood that only the relevant steps of the algorithm are discussed in relation to FIG. 1, but that other software-implemented instructions may be needed to control and manage the overall operation of the system. The algorithm or portions of the algorithm may be stored on one or more types of computer-readable medium associated with the instrument 220 and/or the processor 250.

The processor 250 also includes a signal output device to output to a user the REM and NREM variances, the threshold, and/or the calculated percentage of REM sleep time intervals with variance above the threshold. As shown in FIG. 2, the output device may be the screen of the laptop computer. The output may also be stored or transmitted via a network to a remote user. The processor 250 may include multiple algorithms that perform various methods described by the present disclosure.

Methods and systems employing the algorithm, performance and output of the algorithm, and determination of one or more STREAM values are illustrated by application of these methods and systems to a group of 23 subjects. Subjects (n=23) may be identified and recruited as described by Consens et al. in "Validation of a polysomnographic score for REM sleep behavior disorder" Sleep 2005; 28(8):993-997. Seventeen subjects are patients and six are control subjects. The seventeen patients carried diagnoses of multiple system atrophy (MSA, n=5), Parkinson's disease (PD, n=6), dementia with Lewy bodies (DLB, n=2), progressive supranuclear palsy (n=3), and sporadic olivopontocerebellar atrophy (n=1). Patients with progressive supranuclear palsy are included to have a group of patients with a neurodegenerative disorder causing Parkinsonian symptoms unassociated with RBD, for comparison with the MSA, PD, and DLB patients. Diagnoses are established by board-certified neurologists who specialize in neurodegenerative disorders. A consultation with sleep medicine specialists may be included as part of the protocol. Normal control subjects, without any specific sleep complaints and with no genetic relationship to the patients, had similar age and sex distributions to those of the patients.

Histories, physical examinations, and polysomnograms are performed as follows. Sleep-oriented clinical histories are performed by either of 2 physicians, board-certified in both sleep medicine and neurology, who are masked to any questionnaire and polysomnographic data. Based on widely-used clinical criteria (as described in American Sleep Disorders Association, "International classification of sleep disorders, revised: Diagnostic and coding manual," Rochester, Minn.: American Sleep Disorders Association, 1997), which at that time did not require polysomnography to assess for RBD, the likelihood of the diagnosis is rated as probable (2), possible (1), or unlikely (0). Patients with a history of frequent, clear dream enactment are rated as "probable," those without nocturnal behavioral episodes as "unlikely," and those with such episodes that are not clearly dream enactment are rated as "possible." Seven subjects had a clinical impression of probable RBD, and for purposes of analyses these are combined with the two subjects who had possible RBD.

Bed partners completed a questionnaire that asked for Likert scale ratings for each of the symptoms that are diagnostic criteria for RBD, as per American Sleep Disorders Association, "International classification of sleep disorders, revised: Diagnostic and coding manual," Rochester, Minn.: American Sleep Disorders Association, 1997. Results are tallied and averaged to determine an overall RBD symptom score that could range from 0 to 1.0.

All subjects underwent laboratory-based polysomnography (PSG) for two consecutive nights. Digital recordings included electroencephalogram (EEG) (C3-A2, C4-A1, O1-A2, O2-A1 by International 10-20 system), chin electromyogram (EMG), electrooculogram (EOG), electrocardiogram, snoring, respiratory effort using piezoelectric belts over the chest and abdomen, airflow at the nose and mouth using thermocouples, and pulse oximetry. Surface EMGs are recorded from the forearm extensor compartments and the anterior tibialis muscles bilaterally. The data are collected using Telefactor digital polysomnography equipment (Conshohocken, Pa.). The EMG is recorded with a 10 Hz high-pass filter and a 60 Hz notch filter, and sampled at 200 Hz. A digital 10-70 Hz band pass filter is applied to the EMG data before subsequent computer processing. Experienced polysomnographic technologists masked to patient diagnoses applied the electrodes, monitored the studies continuously, and monitored the subjects by continuous video observation.

Polysomnograms are scored manually according to a standard protocol, as described in Rechtschaffen A, Kales A, "A manual of standardized terminology, techniques and scoring system for sleep stages of human subjects," Los Angeles: Brain Information Service/Brain Research Institute, UCLA, 1968. In addition, one senior registered polysomnographic technologist masked to patients' clinical data manually (visually) scored PSG measures of RBD in accordance with the approach described by Lapierre O, Montplaisir J., "Polysomnographic features of REM sleep behavior disorder: Development of a scoring method," Neurology 1992; 42:1371-1374. The approach is based on two measurements: the proportion of 20-second REM sleep epochs that contain a predominance of abnormally elevated background chin muscle tone (tonic component), and the proportion of 2-second mini-epochs (within 20-second REM sleep epochs) that show bursts of EMG activity (phasic component). Identical measures are used with the present methods, except that the epochs to assess tonic activity are 30 seconds in duration (a more widely used standard), and the mini-epochs to assess phasic activity are 3 seconds in duration. Each REM sleep epoch is scored as tonic or atonic depending on whether tonic chin EMG activity is present for more or less than 50% of the epoch.

"Percent phasic" and "percent tonic" scores for each subject are computed as a REM sleep duration-weighted average of the results from the two nights, in a manner that essentially considered the data from the two recordings as if they are obtained from one long night. The percent phasic and percent tonic scores are then averaged to obtain an overall "PSG score" that reflects results of the visually-assessed method described by Lapierre O, Montplaisir J., "Polysomnographic features of REM sleep behavior disorder: Development of a scoring method," Neurology 1992; 42:1371-1374.

A computer algorithm is used to calculate the variance of the chin EMG signal during all 3-s mini-epochs within each PSG. The variance σ is computed as:

$$\sigma = 1/(N-1)\sum_{i=1}^{N}(x_i - \bar{x})^2$$

where N is the number of samples in the interval, $x_i$ is the ith data sample in the interval, and $\bar{x}$ is the mean of the samples in the interval. If the variance calculation is replaced by the sum of the square amplitudes, similar results may be obtained. However, the variance calculation is used to generate the results presented. An upper limit for normal EMG background activity during REM sleep is defined as four times the $5^{th}$ percentile of the variance observed during all NREM epochs. Normally, EMG tone during REM sleep should not exceed the lowest tone noted during NREM sleep, operationalized here as the $5^{th}$ percentile of the NREM EMG variance. To identify activity likely to be abnormal, with reference to NREM EMG tone, a cut-off at 4 times the $5^{th}$ percentile is initially tested. Other cut-offs may perform similarly; e.g., 2 to 6 times the $5^{th}$ percentile. The percentage of REM mini-epochs with variance above the selected threshold is computed as the new metric, referred to as the Supra-Threshold REM EMG Activity Metric (STREAM). Since STREAM is the percentage of REM mini-epochs with variance above the selected threshold, it does not have units. A score for each subject is calculated as a REM sleep duration-weighted average of the results from the 2 nights.

Associations are tested for significance with the nonparametric Spearman correlation coefficient rho, to avoid the assumption that underlying distributions of variables were normal. Receiver-operator curves were used to assess performance of the new metric in comparison to the visual methods of Lapierre and Montplaisir. The level of statistical significance is set at $p<0.05$.

Results are as follows. The 23 subjects had a mean age of 63±10 (s.d.) years and 12 were women. Table 1 below shows for each subject the RBD PSG score, EMG variance on each night, overall EMG variance score, STREAM on each night, overall RBD symptom score, and clinical impression based on criteria established by the International Classification of Sleep Disorders (ICSD). The mean STREAM was 22.59±19.42. An example of EMG variance results during one 30-second epoch is shown in FIG. 3. The change in EMG variance through the night is illustrated in FIG. 4 for two representative subjects, one with and one without RBD based on clinical impression. For the patient without RBD (FIG. 4 panel A, in red), the computed EMG variance is generally below the threshold during REM sleep, whereas for the patient with RBD (FIG. 4 panel B, in green), the EMG variance often exceeds the threshold.

FIG. 3 graphically illustrates a thirty-second epoch of REM sleep recorded from subject 7 (upper panel), along with a corresponding plot of calculated EMG variance for each 3-second mini-epoch (lower panel); LOC-A2 and ROC-A1 are left and right electro-oculograms; Chin1-Chin2 is the submental EMG signal; C3-A2, C4-A1, O1-A2, and O2-A1 are left central, right central, left occipital, and right occipital EEG derivations; the dashed line labeled "Threshold" is placed at 4 times the $5^{th}$ percentile value of non-REM chin electromyographic variance for this particular subject;

FIG. 4 graphically illustrates electromyographic variance computed over 3-second mini-epochs though the night (A) for a subject without a clinical diagnosis of RBD (subject 17), and (B) for a subject with a clinical diagnosis of RBD (subject 2); NREM (blue) signifies values associated with non-REM mini-epochs; REM<THRES (red) indicates REM mini-epochs with EMG variance values less than the 4 times the non-REM 5$^{th}$ percentile threshold, and REM>THRES (green) indicates REM epochs with EMG variance greater than the threshold;

TABLE 1

Summary of RBD Measures for Each Subject*

| Subject | PSG Score | STREAM Night 1 | STREAM Night 2 | STREAM (2-night weighted average) | ICSD-Based Clinical Impression | RBD Symptom Score |
|---|---|---|---|---|---|---|
| 1 | 11.86 | 8.82 | 11.25 | 10.41 | 0 | 0.586 |
| 2 | 59.34 | 5.96 | 63.70 | 38.28 | 2 | 0.623 |
| 3 | 57.45 | 14.67 | 15.27 | 15.22 | 2 | 0.643 |
| 4 | 14.25 | 37.87 | 13.80 | 23.39 | 2 | 0.586 |
| 5 | 43.14 | 45.79 | 54.00 | 49.39 | 2 | 0.671 |
| 6 | 68.20 | 50.28 | 46.67 | 49.55 | 0 | 0.308 |
| 7 | 50.92 | 47.83 | 52.06 | 50.55 | 1 | 0.521 |
| 8 | 37.26 | 26.43 | 12.32 | 20.13 | 0 | 0.29 |
| 9 | 5.88 | 21.65 | 15.97 | 18.85 | 0 | 0.41 |
| 10 | 64.99 | 54.62 | 37.86 | 44.26 | 2 | 0.65 |
| 11 | 59.16 | 82.07 | 59.90 | 72.20 | 0 | 0.21 |
| 12 | 0.72 | 1.98 | 0.99 | 1.43 | 0 | 0.353 |
| 13 | 9.14 | 3.33 | 15.54 | 15.06 | 1 | 0.532 |
| 14 | 9.96 | 7.21 | 4.80 | 5.71 | 0 | 0.35 |
| 15 | 46.30 | 32.10 | 27.34 | 29.67 | 2 | 0.79 |
| 16 | 12.76 | 2.91 | 94.26 | 26.18 | 2 | 0.592 |
| 17 | 1.98 | 2.05 | 2.86 | 2.48 | 0 | 0.275 |
| 18 | 14.79 | 21.26 | 5.39 | 14.99 | 0 | 0.21 |
| 19 | 10.24 | 3.43 | 4.45 | 4.01 | 0 | 0.241 |
| 20 | 2.03 | 5.45 | 1.75 | 3.28 | 0 | 0.208 |
| 21 | 5.19 | 13.18 | 4.76 | 8.64 | 0 | 0.28 |
| 22 | 3.64 | 8.05 | 3.83 | 5.38 | 0 | 0.583 |
| 23 | 6.23 | 9.84 | 11.06 | 10.43 | 0 | 0.208 |

*RBD = REM sleep behavior disorder; PSG = polysomnogram; STREAM = supra-threshold REM electromyographic (EMG) activity metric; ICSD = International Classification of Sleep Disorders.

As shown in FIG. 5, the variance-based STREAM correlates well with the visually-derived PSG score for RBD severity (Spearman rho=0.85, p<0.0001). The result is similar even if the analysis is confined to the 17 subjects with neurodegenerative disorders (rho=0.82, p=0.0001). A clinical impression of RBD (probable or possible, n=9 subjects) is associated to a similar extent with both the computer-generated STREAM (Wilcoxon rank sum test, p=0.0089) and the visually-derived PSG score (p=0.0182). Subjects without a clinical diagnosis of RBD are indicated by circles (o), and the subjects with a clinical diagnosis of possible or probable RBD are indicated by crosses (x);

FIG. 6 shows that both the STREAM and the PSG score effectively separate subjects with and without an ICSD-based clinical impression of probable or possible RBD. Using the optimal threshold levels (12% for the PSG score and 14% for the EMG variance score) the methods have sensitivities of 89% for the PSG score and 100% for the STREAM, and specificity of 71%, with 78% (18 of the 23) patients classified correctly using the PSG score and 83% (19 of 23) patients classified correctly using the STREAM. Panel A illustrates the computer-generated EMG variance score and Panel B illustrates the visually-generated PSG score (B), where both show similar ability to separate subjects for whom RBD was considered probable or possible (1) or unlikely (0) by clinicians who interviewed and examined the subjects; box plots show median, 25th and 75th percentiles as horizontal lines; the whiskers extend from the box out to 1.5 times the interquartile range of the data; the '+' marks show outliers; panel (B) is adapted from methods and described in Example A.

Figures 7A, 7B:
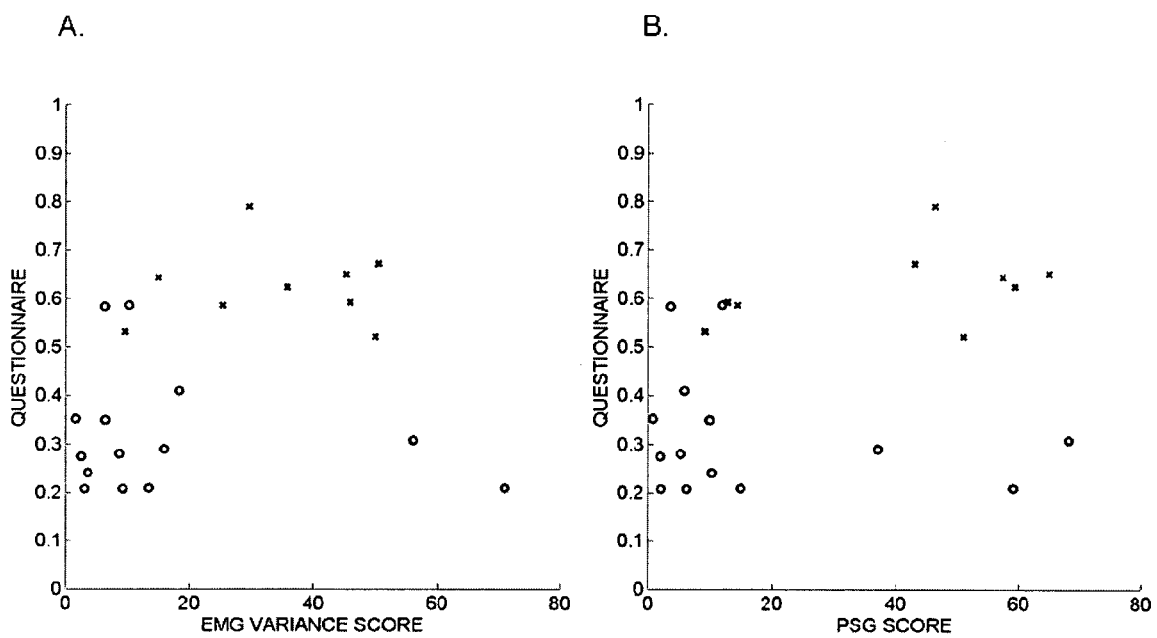

As depicted in FIG. 7, the RBD symptom score correlates to a similar extent, though not strongly, with the computer-generated STREAM (rho=0.42, p=0.046) and the visually-derived PSG score (rho=0.42, p=0.048). RBD symptom scores derived from an International Criteria for Sleep Disorders-based questionnaire are plotted against the computer-generated STREAM score (A) and the visually-generated PSG score (B). Subjects without a clinical diagnosis of RBD are indicated by circles (o), and the subjects with a clinical diagnosis of possible or probable RBD are indicated by crosses (x). Two outliers with high STREAM and low RBD symptom scores appear in FIG. 7A. Review of these polysomnograms shows that in one case, the EMG channel used by the algorithm shows relatively invariant, high activity throughout Night 1 that may be in part artifactual. In the second case, REM sleep is particularly difficult to score because it often resembled wakefulness. Such challenges can be common in a sample of patients with RBD. Elimination of those two outliers from the analysis improves the correlation between the STREAM and RBD symptom score (rho=0.67, p=0.0008).

Both the STREAM and the PSG score can be used as metrics for identifying patients with RBD. A graphical method of summarizing the detection performance obtained with these metrics is to plot a receiver operating characteristic (ROC) curve, which summarizes the tradeoff between sensitivity and specificity for various threshold levels of the metric. Sensitivity represents the probability of detecting RBD when it is present, and specificity represents the probability of not detecting RBD when it is actually absent. An ROC curve comparing the empirical detection performance of the STREAM with the PSG score, for a range of possible threshold values on each measure, reveals similar efficacy for the two approaches, as shown in FIG. 8. FIG. 8 graphically illustrates the receiver-operator characteristic (ROC) curves for the STREAM and the visually-generated PSG score, suggesting similar diagnostic utility for the two approaches; the area under the ROC curves computed using the trapezoidal method is 0.84 for STREAM and 0.73 for the PSG score.

FIG. 9 graphically illustrates that the STREAM during REM sleep on night 1 correlates with STREAM on night 2

(rho=0.53, p=0.0098); subjects without a clinical diagnosis of RBD are indicated by circles (o), and the subjects with a clinical diagnosis of possible or probable RBD are indicated by crosses (x). Among all subjects, the computed STREAM on Night 1 correlates well with the STREAM on Night 2 (rho=0.53, p=0.0098; FIG. 9A); however, this correlation is not as high as that observed for Night 1 and Night 2 visually-derived PSG scores (rho=0.92, p<0.0001). The score from the second night, in comparison to that of the first night, seems to show stronger associations with clinical measures. Specifically, the second night STREAM effectively separates subjects with and without an ICSD-based clinical impression of probable or possible RBD (Wilcoxon rank sum test, P=0.0028), whereas the first night STREAM does not (Wilcoxon rank sum test, P=0.361, FIG. 9B). Similarly, the second night STREAM shows a significant correlation with the RBD symptom score (rho=0.52, P=0.011), but the first night STREAM does not (rho=0.18, P=0.409, FIG. 9C).

The value of the specific EMG frequency content used to compute STREAM is demonstrated by repeating the analyses using narrower, digitally filtered EMG frequency bands. The results, summarized in Table 2 below, suggest that the STREAM computed from lower frequency components of the EMG signal may provide a better association with clinical measures.

in-home sleep studies, where objective evidence for RBD may improve assessment of patients suspected to have RBD, conditions strongly associated with RBD (such as Parkinson's disease, multiple system atrophy, and narcolepsy), or sleep disorders sometimes associated with RBD (such as restless legs syndrome and obstructive sleep apnea).

Some previous attempts to quantify visual scoring of REM EMG activity have focused on bursts of phasic REM activity. "Phasic" refers to rapid eye movements during REM sleep. Such approaches that focus on phasic bursts of muscle activity have identified 5.0 to 12.5% of phasic REM sleep as containing these bursts. The STREAM often identifies higher proportions of REM sleep as having excessive tone, even in most subjects without RBD, and the percent of mini-epochs thus identified on any given night reached a maximum of 81%. These observations suggest that STREAM may assess bursts of activity (see FIG. 3) somewhat smaller in amplitude than those assessed using visual scoring methods. One important advantage of STREAM in comparison to other approaches is that it obviates the need for somewhat arbitrary distinction of tonic and phasic types of motor activity.

Other features of the present methods employing the automated algorithm that may facilitate assessment of RBD features include the automatic identification of a scoring threshold specific to each subject, based on his or her lowest NREM

TABLE 2

Dependence of STREAM, and its Associations with Clinical Measures, on EMG Frequency.

| EMG Frequency | STREAM Combined Nights | ICSD-Based Clinical Impression (Rank Sum Test) P - value | | | RBD Symptom Score (Spearman Correlation) rho (P - value) | | | Spearman Correlation of $1^{st}$ and $2^{nd}$ Night STREAM |
|---|---|---|---|---|---|---|---|---|
| Content Hz | mean ± SD | Comb. | $1^{st}$ Night | $2^{nd}$ Night | Comb. | $1^{st}$ Night | $2^{nd}$ Night | rho (p - value) |
| 10-70 | 22.59 ± 19.42 | 0.0089 | 0.3610 | 0.0028 | 0.42 (0.046) | 0.18 (0.4086) | 0.52 (0.0111) | 0.53 (0.0098) |
| 10-14.9 | 23.58 ± 20.62 | 0.0128 | 0.2439 | 0.0128 | 0.60 (0.0026) | 0.39 (0.0650) | 0.60 (0.0025) | 0.71 (0.0002) |
| 15-19.9 | 22.50 ± 18.24 | 0.0153 | 0.5923 | 0.0061 | 0.48 (0.0194) | 0.24 (0.2704) | 0.45 (0.0296) | 0.42 (0.0461) |
| 20-24.9 | 23.38 ± 18.08 | 0.0253 | 0.7290 | 0.0051 | 0.39 (0.0639) | 0.11 (0.6277) | 0.47 (0.0244) | 0.39 (0.0680) |
| 25-29.9 | 27.98 ± 20.74 | 0.0215 | 0.5923 | 0.0128 | 0.38 (0.0768) | 0.04 (0.8402) | 0.45 (0.0314) | 0.49 (0.0180) |
| 30-34.9 | 30.33 ± 22.99 | 0.0215 | 0.3289 | 0.0128 | 0.38 (0.0755) | 0.12 (0.5804) | 0.43 (0.0405) | 0.58 (0.0045) |
| 35-39.9 | 29.90 ± 23.51 | 0.0547 | 0.3289 | 0.0215 | 0.29 (0.1745) | 0.15 (0.4922) | 0.39 (0.0635) | 0.77 (<0.0001) |
| 40-44.9 | 29.31 ± 23.11 | 0.0631 | 0.3610 | 0.0253 | 0.28 (0.1951) | 0.08 (0.7013) | 0.37 (0.0842) | 0.78 (<0.0001) |
| 45-49.5 | 30.29 ± 23.01 | 0.0726 | 0.3610 | 0.0182 | 0.27 (0.2208) | 0.10 (0.6551) | 0.42 (0.0456) | 0.78 (<0.0001) |
| 50-54.9 | 30.15 ± 22.61 | 0.0631 | 0.2439 | 0.0153 | 0.27 (0.2102) | 0.15 (0.4994) | 0.40 (0.0579) | 0.83 (<0.0001) |
| 55-59.9 | 29.26 ± 23.15 | 0.0298 | 0.2193 | 0.0182 | 0.32 (0.1393) | 0.15 (0.4808) | 0.39 (0.0635) | 0.81 (<0.0001) |
| 60-64.9 | 29.10 ± 23.52 | 0.0298 | 0.1227 | 0.0182 | 0.32 (0.1419) | 0.17 (0.4284) | 0.38 (0.0723) | 0.83 (<0.0001) |
| 65-70 | 31.41 ± 23.85 | 0.0406 | 0.2193 | 0.0253 | 0.31 (0.1582) | 0.13 (0.5558) | 0.37 (0.0824) | 0.84 (<0.0001) |

Embodiments of the present methods applied to the sample of patients with neurodegenerative disorders and control subjects demonstrates that computerized analysis of EMG variance during sleep quantifies polysomnographic evidence of RBD about as effectively as did a previously validated and commonly used visual scoring method. Both approaches appear to be effective in separating subjects with RBD from subjects without RBD. Major differences between the present methods employing computerized analysis as compared to visual RBD scoring, include the following: the present methods produce results in seconds rather than 1-3 hours for typical visual scoring; no previous experience in specialized RBD scoring is required for the present methods; the present methods may provide substantial cost savings; and the present methods may eliminate concerns over test-retest, inter-scorer, or inter-laboratory reliability. The automatic computation of STREAM may be used in research settings requiring quantification of polysomnographic evidence for RBD. The algorithm also may prove useful in clinical laboratory-based or muscle activity. A subject's discomfort, restlessness, periodic leg movements, sleep apnea, or immobility (e.g., secondary to Parkinson's disease) could well affect average EMG variance. So could the quality of the connection between the EMG electrode and the skin over the muscle to be recorded. Hence, the REM EMG-scoring threshold may be based on the $5^{th}$ percentile (low end) of the non-REM variance for the specific individual and his or her specific sleep study to assure that only minimum non-REM muscle tone during quiet sleep is used in all cases to determine the threshold for excessive REM sleep muscle tone.

The so-called "first night effect" in polysomnography may affect REM sleep prominently and might explain the observation that the second night of polysomnography, in comparison to the first night, seems more useful in automatic assessment for RBD. The original approach was to combine data from the 2 nights because REM sleep can be brief or difficult to score in older patients and especially those with neurodegenerative conditions. Two nights of diagnostic recording are already advocated by some for patients suspected to have parasomnias. The present data support this approach, or else a habituation night of unrecorded sleep in a laboratory setting prior to the actual recording.

Several modifications to the EMG variance algorithm are possible. For example, the decision to use four times the non-REM 5$^{th}$ percentile for EMG variance as the threshold during REM sleep produces a reasonably wide spread of results between subjects with and without RBD, but other thresholds may be used to increase or decrease the spread. Moreover, whereas one chin EMG derivation is used for each subject, more selective attention to the derivation with the best signal quality may improve results, for example as suggested by the review of outlier data. Alternative sites, in addition to or in combination with the chin site, may also be used for recording the surface EMG. The chin can be a good initial choice because the differences in muscle tone during REM and NREM sleep at this site can be greater than those recorded over muscles in any extremity. For example, exploration of other sites shows a correlation with clinical measures for the left anterior tibialis as a recording site. Thus, the present algorithms and thresholds may be optimized for use at one or more sites.

In some embodiments, the present methods and systems may be applied to patients with idiopathic RBD. For example, patients with idiopathic RBD may develop one of the neurodegenerative conditions examined using the present methods and RBD manifestations in patients with and without neurodegenerative conditions are largely indistinguishable. In some embodiments, the present algorithm does not exclude EMG bursts at the termination of apneic events, and in other embodiments the method and algorithm performance may be enhanced if such EMG bursts are excluded. Additionally, in some embodiments specific EMG frequency bands may prove more useful than others. For example, the lower frequency bands examined (e.g., 10 to 15 Hz) appear to be more useful, and frequencies lower than 10 Hz may perform better in some embodiments.

The present disclosure also includes the following features. The patient and study-specific non-REM sleep EMG variance can be used to determine a threshold above which REM sleep EMG tone should not normally rise; that this level of activity is computed automatically by the algorithm; and that the diagnosis of RBD (or identification of REM sleep without atonia) can be facilitated by analysis of the frequency with which the EMG minimum variance threshold established during non-REM sleep is in fact exceeded during REM sleep. In some embodiments, the effective quantitative analysis of the EMG during REM sleep can be performed with one single assessment of EMG activity, rather than the two separate assessments that are employed visually in traditional, manual assessments of polysomnograms for evidence of RBD. Other approaches—either non-quantitative as described in the International Classification of Sleep Disorders or quantitative but visual and subjective as described by LaPierre and Montplaisir (Neurology, 1992)—all rely on separate assessments of REM sleep-associated discrete bursts of EMG activity and baseline EMG tone. In the present methods, one single synthesized quantitative assessment of EMG variance during REM sleep may be as effective as the more complicated dual approach, which appears to be unnecessary.

The present methods include polysomnographic assessment for REM sleep behavior disorder (RBD). These methods may be used in conjunction with visual scoring methods which are reliable but require slow, labor-intensive visual scoring of surface electromyogram (EMG) activity. The present methods and systems may include a computerized metric to assess EMG variance where this metric may be used alone or in conjunction with results from visual scoring, bed partner-rated RBD symptom scores, and/or clinical assessments by sleep medicine specialists.

The present methods correlate well with visual quantitative scoring methods. Nocturnal polysomnograms are acquired for each subject. A computer algorithm calculates the variance of the chin EMG during all 3-second mini-epochs, and compares variances during REM sleep to a threshold defined by variances during quiet non-REM (NREM) sleep. The percentage of all REM mini-epochs with variance above this threshold creates a metric, which is referred to as the suprathreshold REM EMG activity metric (STREAM) for each subject. The STREAM correlates highly with the visually-derived score for RBD severity (Spearman rho=0.87, P<0.0001). A clinical impression of probable or possible RBD was associated to a similar extent with both STREAM (Wilcoxon rank sum test, P=0.009) and the visually-derived score (P=0.018). An optimal STREAM cutoff identified probable or possible RBD with 100% sensitivity and 71% specificity. The RBD symptom score correlated with both STREAM (rho=0.42, P=0.046) and the visual score (rho=0.42, P=0.048). The present methods and systems for assessment for RBD provide as much or more utility as compared with the more time-consuming manual visual scoring approach.

The present methods and systems include providing EMG scoring methods in order to distinguish RBD patients from control subjects. In some embodiments, these methods may be used to validate other methods or may be performed in combination with features of other quantitative methods as described by Lapierre O, Montplaisir J., "Polysomnographic features of REM sleep behavior disorder: Development of a scoring method," Neurology 1992; 42:1371-1374, including those methods as described in Examples 1 and 2. For example, the present methods and systems may be combined with those described by Consens F B, Chervin R D, Koeppe R A et al., "Validation of a poly somnographic score for REM sleep behavior disorder," Sleep 2005; 28(8):993-997 that demonstrate the diagnostic validity of the polysomnographic score. The present methods therefore may serve to augment or replace limitations of such visual scoring methods, where using visual scoring methods alone is hampered by subjectivity, time-consumption (typically adding 1-3 hours to total scoring time), expense, and where visual scoring is feasible only after considerable practice by an experienced technologist.

The present methods and systems include a computer algorithm that compares EMG variance during REM and NREM sleep and generates a score predictive of RBD symptoms, ICSD-based diagnoses, and visual polysomnographic findings. These methods and systems reduce time and labor and increase reliability of efforts to identify or quantify RBD features on polysomnography. These methods and systems may be used for clinical diagnosis or assessment for RBD or for evaluation of patients who have conditions in which the risk of RBD is increased. In some cases, the present methods and/or combination of methods can provide EMG scoring that distinguishes RBD patients from control subjects.

EXAMPLE 1

Example 1 illustrates quantitative visual scoring methods that may be used comparatively or in conjunction with the present methods that include an algorithm that compares EMG variance during REM and NREM sleep and generates a score predictive of RBD symptoms, ICSD-based diagnoses, and visual polysomnographic findings. These visual scoring methods include methods and modifications of the methods as described by Consens F B, Chervin R D, Koeppe R A et al., "Validation of a poly somnographic score for REM sleep behavior disorder," Sleep 2005; 28(8):993-997.

Subjects are selected as follows. Patients have diagnoses of multiple system atrophy (MSA), Parkinson disease (PD), dementia with Lewy bodies (DLB), progressive supranuclear palsy (PSP), or sporadic olivopontocerebellar atrophy (OPCA). Diagnoses are made by board-certified neurologists who specialize in neurodegenerative disorders. The patients are volunteer participants in a National Institutes of Health-funded study of RBD in the α-synucleinopathies, including MSA, PD, and DLB. They are recruited from the ataxia, movement disorders, and cognitive disorders clinics at the Department of Neurology, University of Michigan. Subjects are recruited sequentially from these clinics if they met criteria for diagnosis; indicated interest in the research study; and signed a consent form or, if demented, had a consent form cosigned by the next of kin or legal guardian. The patients had not previously been referred to a sleep disorders center, and a consultation with sleep experts is included as part of their study. Patients with PSP are included to have a group of patients with a neurodegenerative disorder causing parkinsonian symptoms unassociated with RBD, for comparison with the MSA, DLB, and PD patients. For comparison to patients with neurodegenerative disorders, normal control subjects with a similar age and sex distribution are included. The controls are individuals not genetically related to the patients but still interested in participating in the study. Control subjects have no neurodegenerative disease. They are recruited from the community and not specifically selected for any sleep complaints. For the most part they shared the same environment as the subjects (significant other, friend, church member, etc.).

The clinical interview of patients is as follows. Subjects are admitted to the General Clinical Research Center Sleep Disorders Laboratory, where they undergo a complete history and physical examination. A comprehensive evaluation of their sleep history is performed by either of 2 neurologists who are each diplomates of the American Board of Sleep Medicine and the American Board of Psychiatry and Neurology. Based on the International Classification of Sleep Disorders (ICSD) entry for RBD, the physicians generate an overall clinical impression of whether the likelihood of RBD is probable, possible, or unlikely. Because evidence-based definitions of these states do not exist, this rating represents a Likert scale only. In general, patients with a history of frequent, clear dream enactment are rated as "probable," those with no history of such episodes as "unlikely," and those with behavioral episodes that are not clearly repeated dream enactment are rated as "possible." At the time of the interview, the clinicians are masked to questionnaire and polysomnographic results but not to any medical history.

The questionnaire information includes the following. All subjects received a questionnaire to be completed by the bed partner. Symptom items reflected each criterion listed in the ICSD; see Table 3 below. When no partner is available, the subjects themselves are asked to complete the questionnaire. Responses for symptom items, which have different numbers of response levels in some cases, are expressed as a proportion of the maximal item value: each response therefore varied from 0 (denied) to 1 (fully endorsed). For example, a response of 2 on item E is converted to a value of 0.50, whereas a response of 2 on item B is converted to a value of 0.25. The average score on all question items then was used as the overall RBD symptom score.

TABLE 3

Questionnaire That Bed Partners Used to Rate The Severity of RBD.

| ICSD Criterion | Scale | Question item |
| --- | --- | --- |
| A | 1-5 | My bed partner has a problem with violent or injurious behavior during sleep |
| B or | 1-5 | My bed partner moves his/her arms, legs, body during dreams |
| C-1 | 1-5 | My bed partner's behavior during sleep is harmful or potentially harmful |
| C-2 | 1-5 | My bed partner appears to act out dreams |
| C-3 | 1-5 | My bed partner's behaviors during sleep disrupt his/her sleep |
| D | 1-4 | How much discomfort does your bed partner's behavior cause you? |
| E | 1-3 | What is the duration of your bed partner's symptoms? |

In Table 3, RBD refers to REM (rapid eye movement) sleep behavior disorder; ICSD, International Classification of Sleep Disorders. Scales for items A-C3 ranged from (1) never to (5) nightly; for item D, from no discomfort (1) to severe discomfort (4); for item E, from less than 1 month (1) to more than 6 months (3).

Sleep studies include the following. All subjects are studied on 2 consecutive nights with laboratory-based polysomnography (PSG). Digital recordings include electroencephalogram (C3-A2, C4-A1, O1-A2, O2-A1 by International 10-20 system), chin EMG, electrooculogram, electrocardiogram, snoring, respiratory effort using piezoelectric belts over the chest and abdomen, and airflow at the nose and mouth using thermocouples. Bilateral surface EMGs from the arms (with electrodes placed over the forearm extensor compartment) and legs (with electrodes placed over the anterior tibialis muscles) are also recorded. Oxyhemoglobin saturation is monitored by pulse oximetry and behavior is monitored by continuous video observation. Experienced polysomnographic technologists masked to patients' diagnoses apply the electrodes and continuously monitor the recordings.

Scoring includes the following. Polysomnographic technologists use 21-inch-high resolution (1600×1200 pixel) computer monitors and standard techniques 17 to score manually all recordings for sleep stages, limb movements and respiratory events. One senior registered polysomnographic technologist masked to patients' clinical data scores PSG measures of RBD according to the method described by Lapierre O, Montplaisir J., "Polysomnographic features of REM sleep behavior disorder: Development of a scoring method," Neurology 1992; 42:1371-1374 (RPSM). Lapierre and Montplaisir suggest that patients with RBD may be distinguished from normal control subjects with 2 measurements: the proportion of 20-second REM sleep epochs that contain a predominance of abnormally elevated background chin muscle tone (tonic component), and the proportion of 2-second mini-epochs (within 20-second REM sleep epochs) that show bursts of EMG activity (phasic component). The instant visual methods employed identical measures except that the epochs to assess tonic activity are 30 seconds in duration (a more widely used standard), and the mini-epochs to assess phasic activity are 3 seconds in duration. Following the RPSM, each REM sleep epoch is scored as tonic or atonic depending upon whether tonic chin EMG activity is present for more or less than 50% of the epoch. No particular exclusions are made when physiologic evidence for REM sleep may not have occupied the entire epoch, or when an arousal (for example, after an apnea) occurred during an epoch scored as REM sleep. After disruption of REM sleep by movement arousals or by artifact, the continuation of rapid eye movements, increased motor activity with erratic behavior, or incongruous vocalizations are used to identify reemergence of REM sleep if the electroencephalogram signal is consistent with REM sleep and alpha frequencies were absent.

Analysis includes the following. Data from both nights of observation are used to calculate a single weighted mean for each of the 2 RBD measures. For example, if 60 epochs of REM sleep are recorded on the first night and 30 epochs on the second night, the first night is weighted by a factor of 2 relative to the second night. If 20% of the 60 epochs recorded on the first night and 50% of the 30 epochs on the second night are abnormal, the weighted average is (0.2×60+0.5×30)/(60+30)=0.3 or 30%, and not simply the average of 20% and 50%, which is 35%. This approach is identical to analyzing the data of the 2 nights as if they were obtained from 1 long night.

The RBD measure for the proportion of epochs containing elevated muscle tone and the measure for the proportion of miniepochs containing burst activity are then averaged to obtain an overall RBD polysomnographic score. This score is used in the main analyses: nonparametric Spearman correlations that test for associations with the RBD symptom score, and t tests that assess for associations with the ICSD-based clinical impression. The level of significance is set at P<0.05.

Results include the following. The quantitative visual scoring method is applied to 23 patients (12 women) aged 48 to 81 years (mean 63±10 [SD]). Seventeen subjects had neurodegenerative diseases, including 1 with OPCA, 2 with DLB, 3 with PSP, 5 with MSA, and 6 with PD. Six normal control subjects (5 women) are aged 49 to 74 years (mean 53±4). Only 1 control subject had no partner and therefore completed her own questionnaire.

Table 4 lists subject ages, sexes, diagnoses, and scores for each RBD measure: polysomnographic, symptom-based, and overall clinical impression. Only 2 subjects are thought by clinicians to have "possible RBD," and these subjects therefore are combined with the "probable" group for analyses. The mean RBD polysomnographic score and component measures are listed in Table 5.

TABLE 5

Polysomnograhic RBD Scores, along with Component Scores: Percentage Phasic and Tonic Measures

| Polysomno-graphic | All subjects* (n = 9) | RBD subjects* (n = 14) | Non-RBD P value | T test |
|---|---|---|---|---|
| RBD Score | 25.89 ± 24.22 | 39.81 ± 21.88 | 16.94 ± 21.85 | 0.02 |
| Phasic, % | 22.10 ± 17.87 | 29.33 ± 19.10 | 17.46 ± 16.02 | 0.12 |
| Tonic, % | 29.67 ± 37.53 | 50.29 ± 41.35 | 16.42 ± 29.13 | 0.03 |

Data are presented as mean±SD. *REM (rapid eye movement) sleep behavior disorder (RBD) defined by clinical impression of possible or probable diagnosis, based on definition in International Classification of Sleep Disorders.

FIG. 10 graphically illustrates a quantitative visual scoring method where the REM (rapid eye movement) sleep behavior disorder (RBD) polysomnographic score (PSG Score) is plotted against the International Classification of Sleep Disorders-based clinical impression of RBD presence (1) or absence (0). Plots show median scores (midline), mean (cross), and 10th, 25th, 75th, and 90th percentiles. The polysomnographic RBD score shows an association with the ICSD-based clinical impression of RBD (t test, P=0.023; FIG. 10). The tonic component of the overall score also shows an association with clinical impression of ICSD (P=0.031). The phasic component is in the expected direction but is not statistically significant (P=0.122).

FIG. 11 graphically illustrates a quantitative visual scoring method where the REM (rapid eye movement) sleep behavior disorder (RBD) polysomnographic score (PSG score) is plotted against the RBD symptom score derived from bed partner questionnaires (Quest). The overall polysomnographic RBD score shows a significant association with the RBD symptom score (Spearman rho=0.42, P=0.048; FIG. 11), as did the

TABLE 4

Summary of Demographic, Diagnostic, and RBD Data.

| Subject | Sex | Age, y | Diagnosis | RBD polysomnographic score | RBD symptom score | ICSD-based clinical impression* | Medications at time of study |
|---|---|---|---|---|---|---|---|
| 1 | M | 81 | PD | 11.85 | 0.59 | 0 | L/C, venlafaxine |
| 2 | M | 74 | PD | 59.33 | 0.62 | 2 | L/C |
| 3 | M | 68 | PD | 57.45 | 0.64 | 2 | L/C, buspirone |
| 4 | M | 65 | PD | 14.25 | 0.59 | 2 | L/C, pramipexole |
| 5 | F | 52 | PD | 43.14 | 0.67 | 2 | L/C, pramipexole |
| 6 | F | 74 | PD | 68.19 | 0.31 | 0 | |
| 7 | M | 60 | MSA | 50.92 | 0.52 | 1 | SSRI |
| 8 | M | 64 | MSA | 37.36 | 0.29 | 0 | |
| 9 | F | 48 | MSA | 5.88 | 0.41 | 0 | |
| 10 | M | 53 | MSA | 64.98 | 0.65 | 2 | SSRI |
| 11 | M | 65 | MSA | 59.16 | 0.21 | 0 | |
| 12 | F | 61 | PSP | 0.72 | 0.35 | 0 | |
| 13 | F | 69 | PSP | 9.14 | 0.53 | 1 | |
| 14 | F | 76 | PSP | 9.96 | 0.35 | 0 | SSRI |
| 15 | M | 66 | DLB | 46.29 | 0.79 | 2 | |
| 16 | M | 78 | DLB | 12.75 | 0.59 | 2 | SSRI: L/C |
| 17 | F | 52 | OPCA | 1.98 | 0.28 | 0 | |
| 18 | F | 58 | NC | 14.78 | 0.21 | 0 | |
| 19 | F | 49 | NC | 10.24 | 0.24 | 0 | |
| 20 | M | 54 | NC | 2.03 | 0.21 | 0 | bupropion |
| 21 | F | 53 | NC | 5.19 | 0.28 | 0 | |
| 22 | F | 57 | NC | 3.64 | 0.58 | 0 | SSRI |
| 23 | F | 74 | NC | 6.23 | 0.21 | 0 | |

*Clinical impression: likelihood of REM (rapid eye movement) sleep behavior disorder (RBD) was probable 2, possible 1, or unlikely 0. PD refers to Parkinson disease; MSA, multiple system atrophy; PSP, progressive supranuclear palsy; DLB, dementia with Lewy bodies; OPCA, sporadic olivopontocerebellar atrophy; NC, normal control; L/C, levodopa/carbidopa; SSRI, selective serotonin reuptake inhibitor.

separate tonic and phasic components of the polysomnographic score (rho=0.49, P=0.018, and rho=0.43, P=0.042, respectively).

The ICSD-based clinical impression of RBD shows a close association with RBD symptom scores (P<0.0001). If a cutoff of 10 or more percentage points on the polysomnographic RBD score is used to indicate RBD (as suggested by receiver-operator curves), the RPSM in comparison with the clinical impression gold standard shows a sensitivity of 89% and a specificity of 57%.

Each of the 23 subjects had some scored REM sleep on each of the two nights, though the amount ranged from 1.5 minutes to 174.5 minutes. Nonetheless, the tonic, phasic, and combined (averaged) measures on night 1 correlate closely with the same measures on night 2 (rho=0.73, P<0.0001; rho=0.83, P<0.0001; and rho=0.92, P<0.0001, respectively).

The quantitative visual scoring measures of RBD polysomnographic features are valid markers for the target sleep disorder. Whether RBD is defined by ICSD-based clinical impressions or by bed-partner symptom ratings, the overall polysomnographic RBD measure shows an association with the presence of the disorder and with its severity. Decomposition of the polysomnographic RBD measure into its component parts—tonic and phasic scores—generates similar results. In addition, the high correlation between polysomnographic RBD measures on nights 1 and 2 reveals little test-retest variability. Together, these results suggest that the Lapierre and Montplaisir approach to quantification of RBD polysomnographic severity is a valid and reliable tool in clinical practice and research.

The previous edition of the ICSD (1992) does not require polysomnographic evidence to meet minimal criteria for the diagnosis of RBD. This supports the use of sleep-specialist clinical impressions and symptom-rating scales as "gold-standards" against which polysomnographic measures are compared. The new ICSD (2005) requires polysomnographic features to confirm the diagnosis. Nevertheless, these polysomnographic features remain, as in the 1992 edition, subjectively determined. A more quantitative method, such as the visual REM sleep polysomnographic scoring method (RPSM), helps to standardize RBD determinations between clinical laboratories, research sites, and polysomnographers at any specific site. Using these methods, the cutpoint of 10% (average of tonic REM percentage and phasic REM percentage) appears to be optimal to define findings suggestive of RBD. However, larger sample sizes may more precisely define an alternate or better cutpoint. Investigation of more healthy individuals may better characterize the normal range of values generated by the RPSM. However, in clinical practice, the distribution of polysomnographic RBD scores is more likely to be unimodal than bimodal, and clinical judgment based on clinical findings along with laboratory results, without a strict cutpoint, may be most useful. In research studies, a well-defined objective cutpoint may help identify a homogenous study sample and improve generalizability of results.

A limitation of quantitative visual scoring is interscorer or intrascorer reliability. An important challenge in patients with α-synucleinopathies is to initially identify REM sleep, the first step in the RPSM. In practice, exceptions to Rechtschaffen and Kales or American Academy of Sleep Medicine (2007) scoring rules must sometimes be made to score REM periods with elevated electromyographic tone despite clear evidence of rapid eye movements and EEG activity consistent with REM sleep. It is not clear whether such exceptions can be made on a reliable basis by different scorers or upon rescoring by the same individual. This limitation could reduce the effectiveness of either visual, Lapierre and Montplaisir-based scoring of RBD features or automated STREAM. An automatic sleep staging algorithm could potentially be used to eliminate inter-rater reliability concerns in REM vs. NREM scoring. The potential for inadequate reliability, and the length of time (up to several hours) required to score nocturnal PSGs with the visual technique, may be reduced also by using the present methods and systems that include a computer algorithm that compares EMG variance during REM and NREM sleep and generates a score predictive of RBD symptoms, ICSD-based diagnoses, and visual polysomnographic findings.

Another potential limitation of quantitative visual scoring arises from combining the percentage of phasic and percentage of tonic measures into 1 overall polysomnographic RBD score. This approach seems logical, when the numbers of studied patients remain somewhat limited, but 1 measure could potentially obscure physiologically informative information in the other. Another potential limitation, as in any initial cross-sectional study, is that results could be sensitive to potential confounds, difficult to assess within the current sample size, such as age, sex, duration of illness, severity of parkinsonian symptoms, or medication status.

RPSM for quantitative visual analysis of polysomnographic RBD features is valid and provides test-retest reliability. The method may be useful in both clinical and research settings. Cutpoints of 10% or more of REM sleep spent with elevated background EMG tone or phasic burst activity suggests a diagnosis of RBD. This quantitative visual method to assess the severity of RBD polysomnographic features is valid and reliable in patients at risk for RBD because of neurodegenerative disorders.

EXAMPLE 2

Example 2 illustrates quantitative visual scoring methods that may be used comparatively or in conjunction with the present methods that include an algorithm that compares EMG variance during REM and NREM sleep and generates a score predictive of RBD symptoms, ICSD-based diagnoses, and visual polysomnographic findings. These visual scoring methods include methods and modifications of the methods as described by Lapierre O, Montplaisir J., "Polysomnographic features of REM sleep behavior disorder: Development of a scoring method," Neurology 1992; 42:1371-1374.

Methods include the following. Patients who fulfill the diagnostic criteria of severe chronic RBD are selected. These patients were referred to the sleep clinic for nocturnal agitation. They exhibit violent behavior during sleep, starting approximately 1 hour after sleep onset and recurring up to five times during the night. These episodes occurred 3 to 7 nights a week for 1 to 4 years. None of the patients reported confusion upon arousal from these nocturnal events, but all reported frequent nightmares characterized mainly by threatening situations in which they would either fight or flee. These nightmares are closely associated with motor behavior responsible for injuries ranging from bruises to wrist fracture.

Five normal controls paired to RBD patients for age (aged 45 to 66 years, mean 58.4) are also included. These control subjects have no clinical evidence of sleep disturbance. In addition, seven patients with idiopathic periodic limb movements in sleep (PLMS) are recorded as controls in order to compare PLMS distribution in REM and non-REM (NREM) sleep with that of RRD patients. Patients and controls are free of psychiatric disorders and epilepsy and none used psychotropic medication for at least 2 months before the study.

Investigation of each patient includes a complete neurologic examination by a neurologist, a routine diurnal EEG, one all-night sleep EEG using Queen Square and parasagittal montages, and CT. In addition, auditory evoked potentials and blink reflexes are assessed to evaluate the integrity of brainstem structures. Results of the neurologic investigation were normal in every subject except for the presence of soft cerebellar signs in one patient. Since RBD had started at an early age (40 years) in this patient, MRI was performed; it revealed an Arnold-Chiari type I malformation.

RRD patients and controls had 2 nights of PSG recording. PSG investigation consists of a standard montage for scoring sleep stages: left and right electrooculograms, submental EMG, central (C3-A2) and occipital (O2-A1) EEG, and ECG. Left and right tibialis anterior EMGs are also recorded and PLMS are scored according to Coleman's criteria (Coleman R M, "Periodic movements in sleep (nocturnal myoclonus) and restless legs syndrome," In Guilleminault C, ed., Sleeping and waking disorders: indications and techniques, Menlo Park, Calif. Addison-Wesley, 1982:265-295). The PLMS index represents the number of periodic limb movements per hour of sleep. During the first night, a nasobuccal thermistor is used to rule out sleep apneas. Apnea is defined as the interruption of oral and nasal airflow for at least 10 seconds. None of the patients or controls exceeded five apneas per hour of sleep. Treatment consisted of clonazepam at dosages varying from 0.5 to 2.0 mg given between 1 and 2 hours before bedtime. Two months after the onset of treatment, patients underwent two additional all-night PSG recordings. Seven idiopathic PLMS controls paired for age were also studied, in order to compare PLMS indexes in REM and NREM sleep with those of RBD patients.

Sleep stages are scored according to a modified version of the method of Rechtschaffen and Kales (Rechtschaffen A, Kales A A, "A manual of standardized terminology, techniques and scoring system for sleep stages of human subjects," Washington, D.C.: US Government Printing Office, Public Health Service, 1968) using 20-second epochs. Since muscle atonia is deficient in RBD patients, REM sleep is scored without submental EMG atonia. The occurrence of the first rapid eye movement is used to determine the onset of a REM sleep period. The termination of a REM sleep period is identified either by the occurrence of specific EEG features (K complexes, sleep spindles, or EEG signs of arousal), or by the absence of rapid eye movements during nine consecutive 20-second epochs. The same method is used to score REM sleep in normal subjects.

The tonic and phasic components of REM sleep are scored separately. Each 20-second epoch is scored as tonic or atonic depending on whether tonic chin EMG activity is present for more or less than 50% of the epoch. Two types of phasic activity characteristic of REM sleep are scored: REM density and phasic EMG density. REM density is defined as the percentage of 2-second mini-epochs of REM sleep containing at least one rapid eye movement. Phasic EMG density is scored from the submental EMG recording and represented the percentage of 2-second mini-epochs containing phasic EMG events. Those phasic EMG events are defined as any burst of EMG activity lasting 0.1 to 5 seconds with an amplitude exceeding four times the background EMG activity. These criteria are used to identify all EMG bursts that clearly contrast with the background activity. Short EMG bursts (less than 100 msec) are not counted, in order to exclude the repetitive discharge from a single motor unit that is found occasionally in normal individuals and in patients during REM sleep and is unaccompanied by any movement on the video recording.

Statistics include the following. A paired t test (two-tailed) for independent variables is used to compare sleep variables of RBD and control subjects. A one-tailed t test is used to compare specific REM sleep features, since the hypothesis was that RHD patients exhibit more tonic and phasic activity during REM sleep. A paired t test (one-tailed) is used to compare data obtained in RBD patients before and after treatment with clonazepam. A Wilcoxon-Mann-Whitney test is performed on variables not normally distributed.

This scoring method shows sensitivity to treatment with clonazepam. An increased phasic submental EMG density occurs in RBD patients, but REM density is similar to that of controls. Clonazepam selectively decreases REM sleep phasic activity but exerts no effect on REM sleep atonia. Periodic limb movements in sleep (PLMS) occur equally in both REM and NREM sleep in RBD patients, suggesting that normal suppression of PLMS in REM sleep is due to motor inhibition.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method for diagnosing and assessing rapid eye movement sleep behavior disorder (RBD) in a patient, comprising:
    measuring at least one physiological signal of the patient during at least one rapid eye movement (REM) sleep time interval and at least one non-rapid eye movement (NREM) sleep time interval;
    determining a REM variance for the physiological signal within the at least one REM sleep time interval and an NREM variance for the physiological signal within the at least one NREM sleep time interval;
    establishing a threshold based on the NREM variance; and
    calculating a percentage of REM sleep time intervals with variance above the threshold, where the steps of determining, establishing and calculating are executed by a computer processor.

2. The method of claim 1, wherein the physiological signal is an electromyogram (EMG).

3. The method of claim 1, wherein the physiological signal is an electrical potential generated by at least one muscle of the patient.

4. The method of claim 3, wherein the at least one muscle is a chin muscle.

5. The method of claim 1, wherein the at least one rapid eye movement (REM) sleep time interval is a plurality of successive time epochs.

6. The method of claim 5, wherein the time epochs are about 3 seconds.

7. The method of claim 1, wherein the measuring includes an automated method for distinguishing REM and NREM sleep time intervals.

8. The method of claim 1, wherein determining at least one of the REM variance or the NREM variance includes using the formula:

$$\sigma = 1/(N-1) \sum_{i=1}^{N} (x_i - \bar{x})^2$$

wherein:
    $\sigma$ is the variance,
    N is a number of samples in the time interval,
    $x_i$ is an ith sample of the signal in the time interval, and
    $\bar{x}$ is mean signal in the time interval.

9. The method of claim 1, wherein determining at least one of the REM variance or the NREM variance includes determining the sum of the square amplitudes of the physiological signal within the at least one REM sleep time interval.

10. The method of claim 1, wherein establishing a threshold based on the NREM variance includes:
setting an upper limit for a physiological signal background during REM sleep, wherein the upper limit is about two to about six times the $5^{th}$ percentile of the NREM variance.

11. The method of claim 10, wherein the upper limit is about four times the $5^{th}$ percentile of the NREM variance.

12. The method of claim 1, wherein the measuring at least one physiological signal of the patient includes signals from two or more nights.

13. The method of claim 1, wherein the measuring at least one physiological signal of the patient occurs following a habituation night of sleep by the patient.

14. The method of claim 1, further comprising classifying the patient as an RBD candidate when the percentage of REM sleep time intervals with variance above the threshold exceeds the threshold during the REM sleep time interval.

15. The method of claim 1, wherein measuring at least one physiological signal of the patient during at least one rapid eye movement (REM) sleep time interval and at least one non-rapid eye movement (NREM) sleep time interval includes filtering the at least one physiological signal.

16. The method of claim 15, wherein the filtering removes a portion of the physiological signal having frequencies greater than about 15 Hz and retains a portion of the physiological signals having frequencies less than about 15 Hz.

17. An automated method for diagnosing and assessing rapid eye movement sleep behavior disorder (RBD) in a patient, comprising:
measuring a physiological signal of the patient during multiple sleep intervals;
identifying portions of the physiological signal which occurred during non-rapid eye movement (NREM) sleep and rapid eye movement (REM) sleep; and
establishing a threshold for the REM portions of the signal using the NREM portions of the signal, where the establishing step is executed by a computer processor.

18. The method of claim 17, wherein the measuring includes measuring an electromyogram (EMG) signal of the patient.

19. The method of claim 17, wherein establishing a threshold includes:
establishing an abnormality threshold for the EMG signal during REM sleep based on variance observed during the NREM sleep portion of the EMG signal; and
computing a percentage of when the REM portions of the EMG signal exceed the abnormality threshold.

20. An automated method for diagnosing and assessing rapid eye movement sleep behavior disorder (RBD) in a patient, comprising:
capturing a electromyogram (EMG) signal while the patient is sleeping;
partitioning the EMG signal into predefined time intervals;
computing a variance for the EMG signal in each time interval using a computer processor, where the variance is a measure from a mean value of the EMG signal; and
computing an indicator of RBD based on the variance measures from the EMG signal using a computer processor.

21. The method of claim 20, further comprising:
establishing an abnormality threshold for the EMG signal during REM sleep based on variance measures observed during a non-REM portion of the EMG signal; and
computing a percentage of when the REM portions of the EMG signal exceeds the abnormality threshold.

22. An automated method for diagnosing and assessing rapid eye movement sleep behavior disorder (RBD) in a patient, comprising:
recording an electromyogram (EMG) signal while the patient is sleeping;
partitioning the EMG signal into predefined time increments and calculating a variance measure for each time increment;
identifying portions of the EMG signal which occurred during non-rapid eye movement (NREM) and rapid eye movement (REM) sleep;
establishing an abnormality threshold for the EMG signal during REM sleep based on variance measures observed during a non-REM portion of the EMG signal; and
computing a percentage of when the REM portions of the EMG signal exceeds the abnormality threshold using a computer processor.

23. The method of claim 22 wherein establishing an abnormality threshold further comprises selecting a variance measure at a fifth lowest percentile of variance measures observed during the non-REM portion of the EMG signal and setting the abnormality threshold to about four times the selected variance measure.

24. The method of claim 22, wherein calculating the variance measure includes using the formula:

$$\sigma = 1/(N-1)\sum_{i=1}^{N}(x_i - \bar{x})^2$$

wherein:
$\sigma$ is the variance,
N is a number of samples in the time increment,
$x_i$ is an ith signal in the time increment, and
$\bar{x}$ is mean signal in the time increment;
or,
determining the sum of the square amplitudes of the signals within the time increment.

* * * * *

UNITED STATES PATENT AND TRADEMARK OFFICE
CERTIFICATE OF CORRECTION

| | |
|---|---|
| PATENT NO. | : 7,996,076 B2 |
| APPLICATION NO. | : 12/080440 |
| DATED | : August 9, 2011 |
| INVENTOR(S) | : Burns et al. |

It is certified that error appears in the above-identified patent and that said Letters Patent is hereby corrected as shown below:

Column 1, line 61, "Variance" should be --variance--.

Column 5, line 1, after "may" insert --be--.

Column 8, line 63, "though" should be --through--.

Column 10, line 39, "shows" should be --show--.

Column 14, line 38, "poly somnographic" should be --polysomnographic--.

Column 15, line 4, "poly somnographic" should be --polysomnographic--.

Column 20, line 65, "RRD" should be --RBD--.

Column 21, line 11, "RRD" should be --RBD--.

Column 22, line 40, Claim 3, "at least one muscle" should be --muscle activity--.

Column 22, lines 42-43, Claim 4, "at least one muscle is a chin muscle" should be --physiological signal is captured on the chin of the patient--.

Column 23, line 54, Claim 20, "a electromyogram" should be --an electromyogram--.

Signed and Sealed this
Sixth Day of March, 2012

David J. Kappos
*Director of the United States Patent and Trademark Office*